(12) United States Patent
    Wiese et al.

(10) Patent No.: US 11,690,589 B2
(45) Date of Patent: Jul. 4, 2023

(54) METHODS AND SYSTEMS FOR WIRELESSLY CHARGING DIGITAL X-RAY DETECTORS

(71) Applicant: GE Precision Healthcare LLC, Wauwatosa, WI (US)

(72) Inventors: Scott Richard Wiese, Wauwatosa, WI (US); Manfred David Boehm, Wauwatosa, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 17/805,627

(22) Filed: Jun. 6, 2022

(65) Prior Publication Data

US 2022/0296201 A1   Sep. 22, 2022

Related U.S. Application Data

(62) Division of application No. 16/871,961, filed on May 11, 2020, now Pat. No. 11,375,973.

(51) Int. Cl.
    *A61B 6/00*  (2006.01)
    *H02J 7/02*  (2016.01)

(52) U.S. Cl.
    CPC ............... *A61B 6/56* (2013.01); *A61B 6/54* (2013.01); *H02J 7/02* (2013.01)

(58) Field of Classification Search
    CPC ... A61B 6/4405; A61B 6/4283; A61B 6/4233; A61B 6/4494; A61B 6/548; A61B 6/4452; A61B 6/54; A61B 6/587; A61B 6/467; A61B 6/566; A61B 6/4411; A61B 6/465; A61B 6/461; A61B 6/4208; A61B 6/42; A61B 6/4007; G01N 23/046; G01N 2223/419; G01N 2201/0221; G01N 2223/301; G01N 2223/1016
    See application file for complete search history.

(56) References Cited

U.S. PATENT DOCUMENTS

| | | |
|---|---|---|
| 10,393,886 B2 | 8/2019 | MacLaughlin |
| 2010/0158197 A1 | 6/2010 | Jadrich et al. |
| 2015/0006395 A1 | 1/2015 | Chu |
| 2018/0220988 A1 | 8/2018 | Jeon |
| 2019/0350543 A1 | 11/2019 | Narayanaswamy et al. |

FOREIGN PATENT DOCUMENTS

| | | | |
|---|---|---|---|
| CN | 102274035 A | * 12/2011 | ........... A61B 6/4494 |
| CN | 105326520 A | 2/2016 | |
| EP | 3145051 A1 | 3/2017 | |

OTHER PUBLICATIONS

European Patent Office, Extended European Search Report Issued in Application No. 21170786.4, dated Sep. 13, 2021, Germany, 8 pages.

* cited by examiner

*Primary Examiner* — Don K Wong
(74) *Attorney, Agent, or Firm* — McCoy Russell LLP

(57) ABSTRACT

Various methods and systems are provided for wirelessly charging a digital x-ray detector of an x-ray imaging system in at least two orientations. In one example, a method comprises: detecting a digital x-ray detector in a charging area of an x-ray system, the charging area including a first power source; pairing the digital x-ray detector to the x-ray system via a wireless connection with the x-ray system; and wirelessly charging the digital x-ray detector via the first power source.

8 Claims, 13 Drawing Sheets

METHODS AND SYSTEMS FOR WIRELESSLY CHARGING DIGITAL X-RAY DETECTORS

CROSS-REFERENCE TO RELATED APPLICATIONS

This application is a divisional of U.S. Non-Provisional application Ser. No. 16/871,961, entitled "Methods and Systems for Wirelessly Charging Digital X-Ray Detectors" filed on May 11, 2020.

FIELD

Embodiments of the subject matter disclosed herein relate to imaging systems, and more particularly, to wirelessly charging accessories of the imaging systems.

BACKGROUND

Imaging systems are widely employed in medical environments, such as hospitals. For example, x-ray imaging systems generate x-rays that are directed toward a subject of interest. The x-rays traverse the subject and impact a film or a digital x-ray detector. For example, the digital x-ray detector may further include a wireless communication module for wirelessly transmitting medical imaging data (e.g., based on an interaction between the x-rays and the subject of interest) to the x-ray imaging system. In particular, the digital x-ray detector may be configured as a portable device, and may include a rechargeable battery for powering the detector, thereby enabling the digital x-ray detector to be operated without an external cable.

For example, in existing systems, digital x-ray detectors may be placed in a charging area (e.g., such as a detector bin, a detector receptor and the like) in a certain orientation in order to undergo charging. For example, for a digital x-ray detector without wireless charging, the detector may be placed in a single orientation in order to enable a wired connection with a power source. Further, existing digital x-ray detectors with wireless charging may only be placed in a single orientation based on placement of a detector battery and wireless power source. For example, a detector may be placed with a non-imaging side closest to a wireless power source to enable charging.

BRIEF DESCRIPTION

In one embodiment, a method comprises detecting a digital x-ray detector in a charging area of an x-ray system, the charging area including a first power source; pairing the digital x-ray detector to the x-ray system via a wireless connection with the x-ray system; and wirelessly charging the digital x-ray detector via the first power source. In this way, a digital x-ray detector may be wirelessly charged without an external cable in at least two orientations, increasing versatility of the digital x-ray detector.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
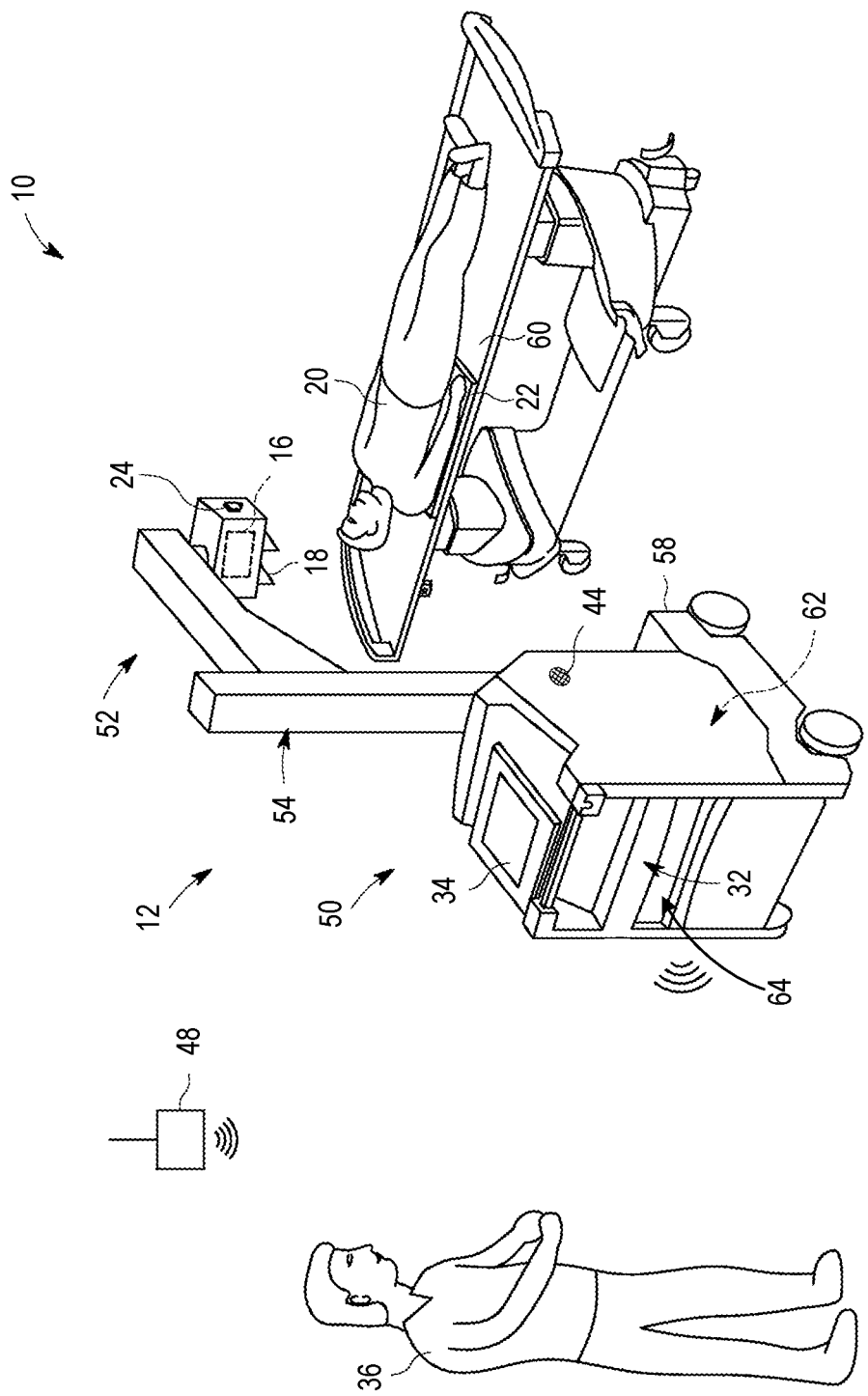
FIG. 1 shows a perspective view of a mobile x-ray system including a digital x-ray detector, according to an embodiment.
Figure 3:
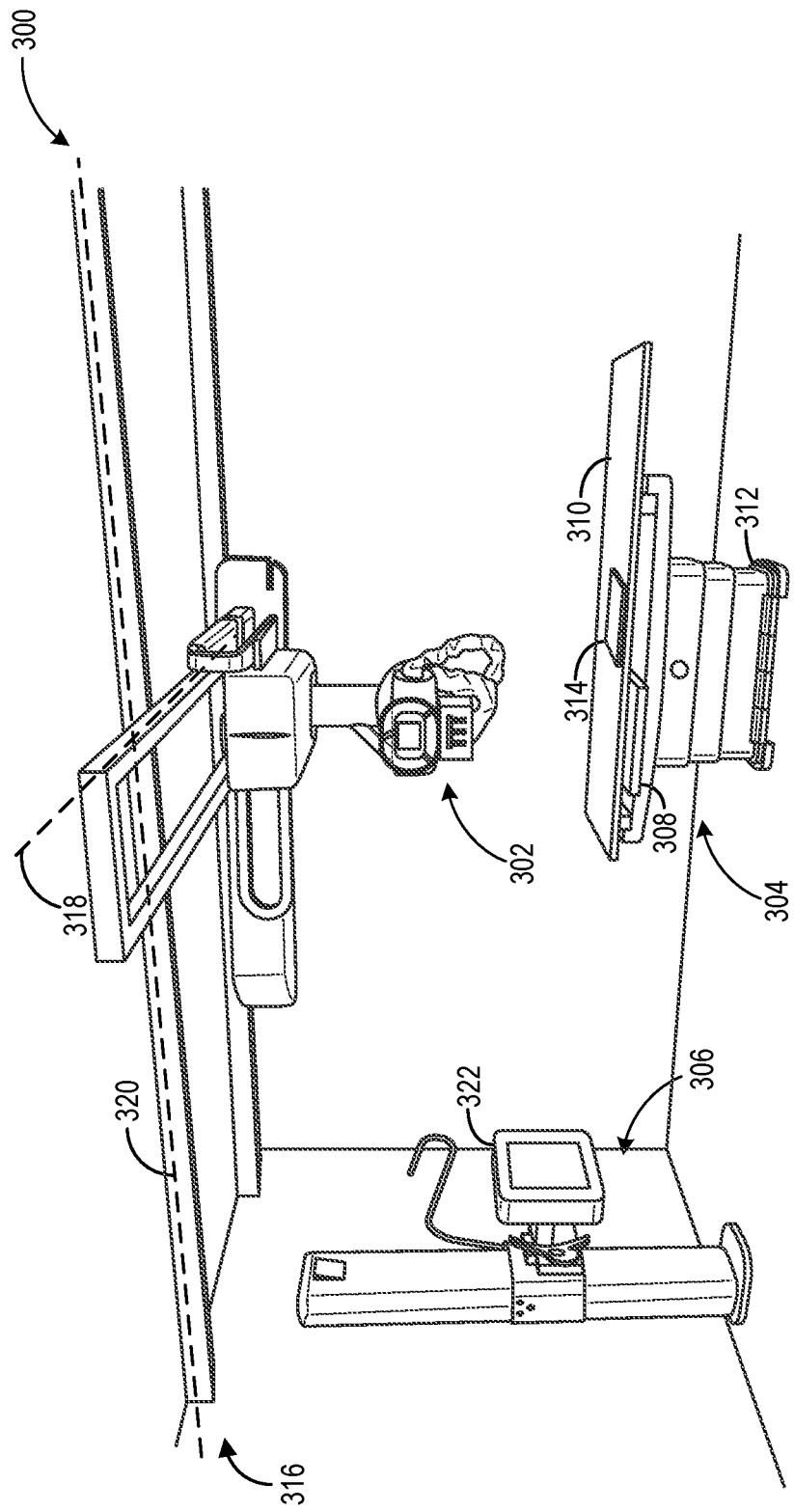
FIG. 3 shows a perspective view of a fixed x-ray system including a digital x-ray detector, according to an embodiment.
Figure 4B:
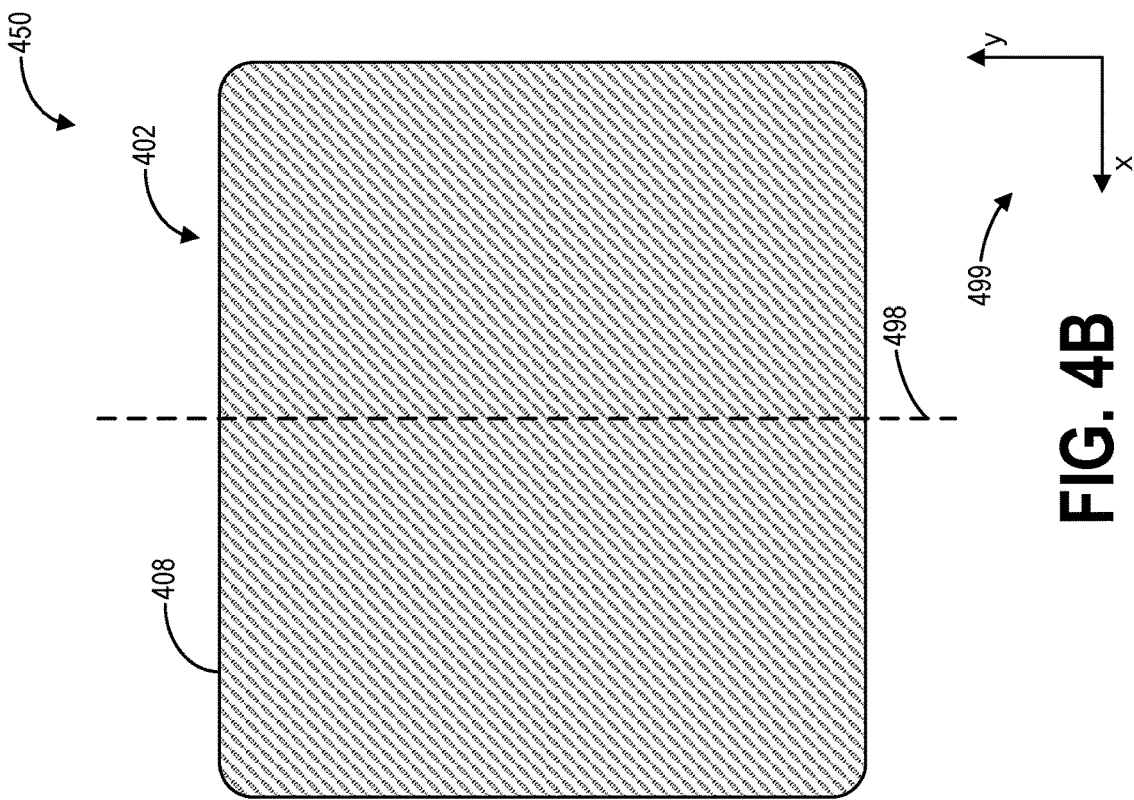
FIG. 4B shows a back view of the digital x-ray detector with wireless charging.
Figure 4A:
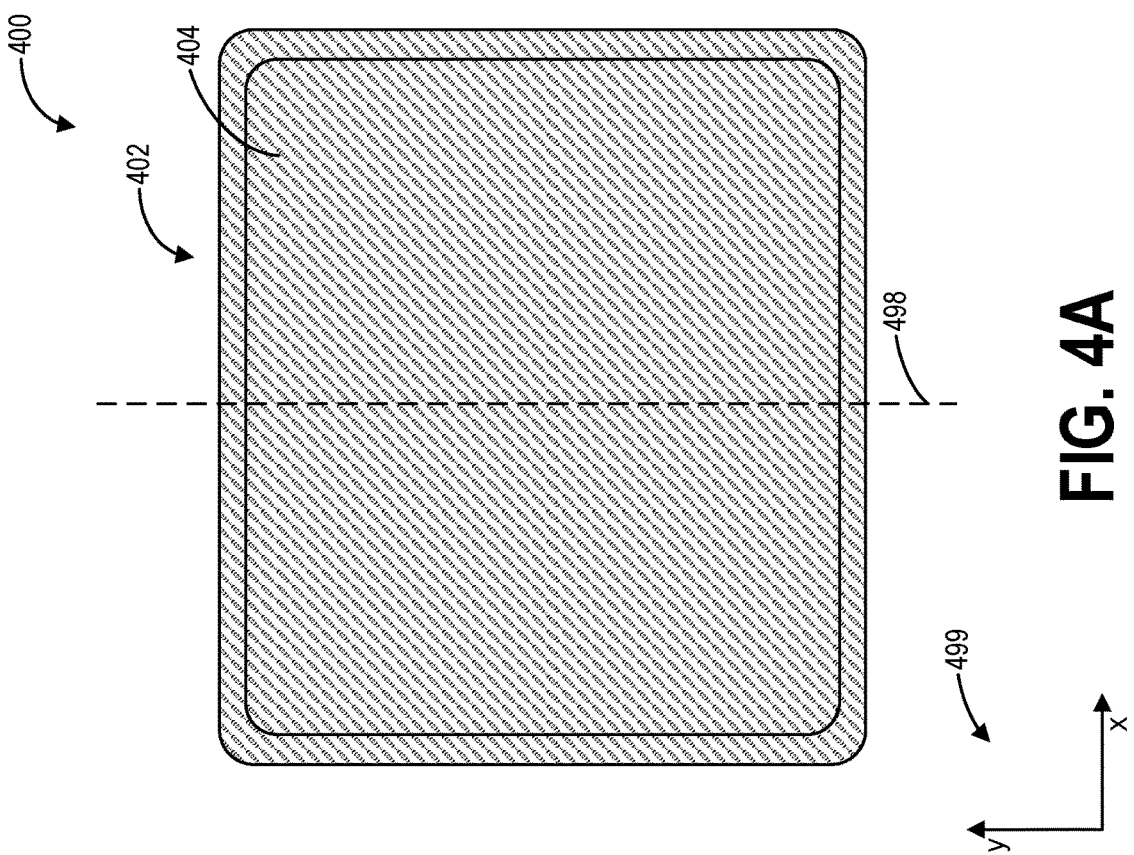
FIG. 4A shows a front view of a digital x-ray detector with wireless charging.
Figure 5:
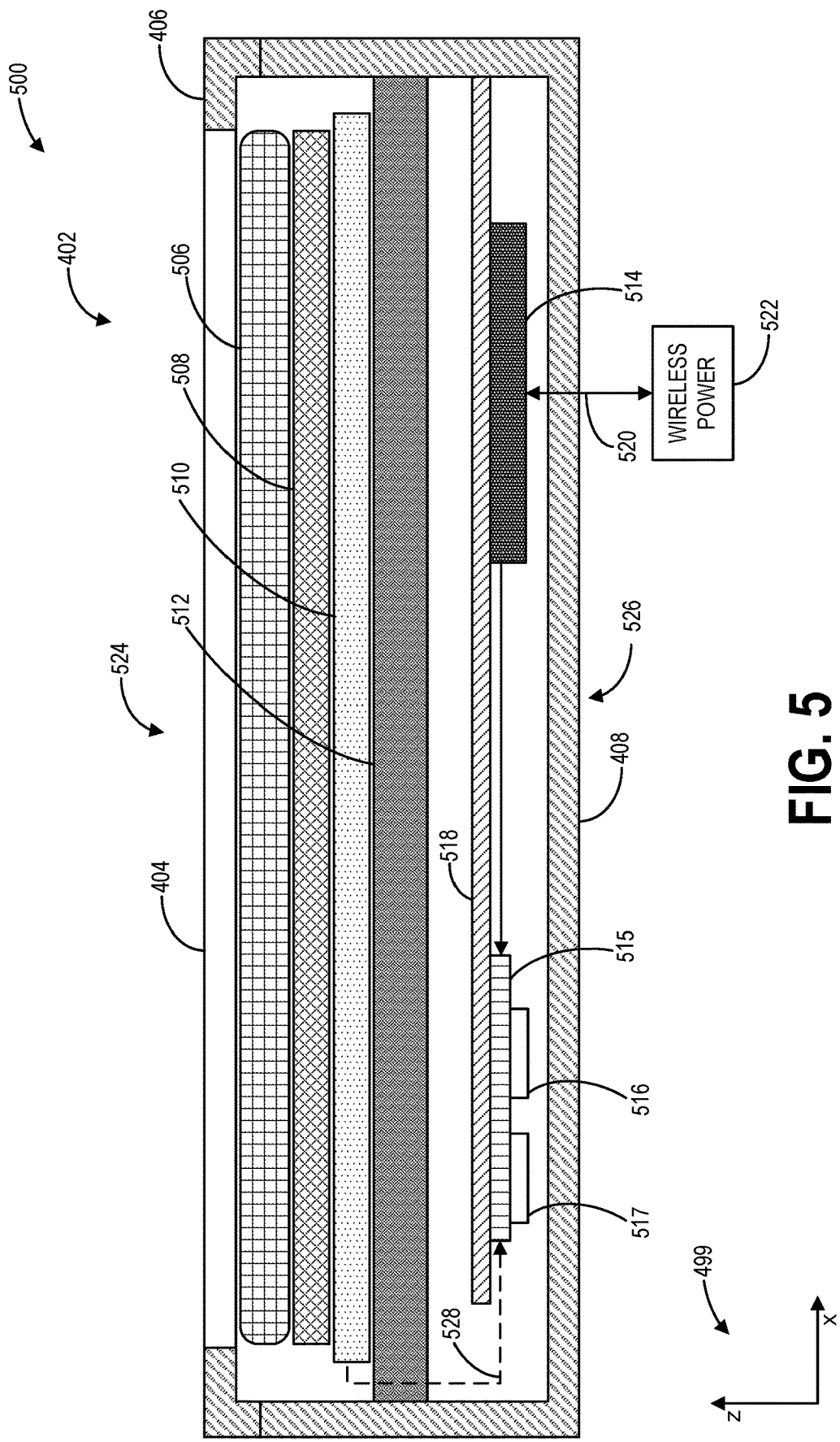
FIG. 5 shows a schematic cross-sectional view of the digital x-ray detector.
Figure 6A:
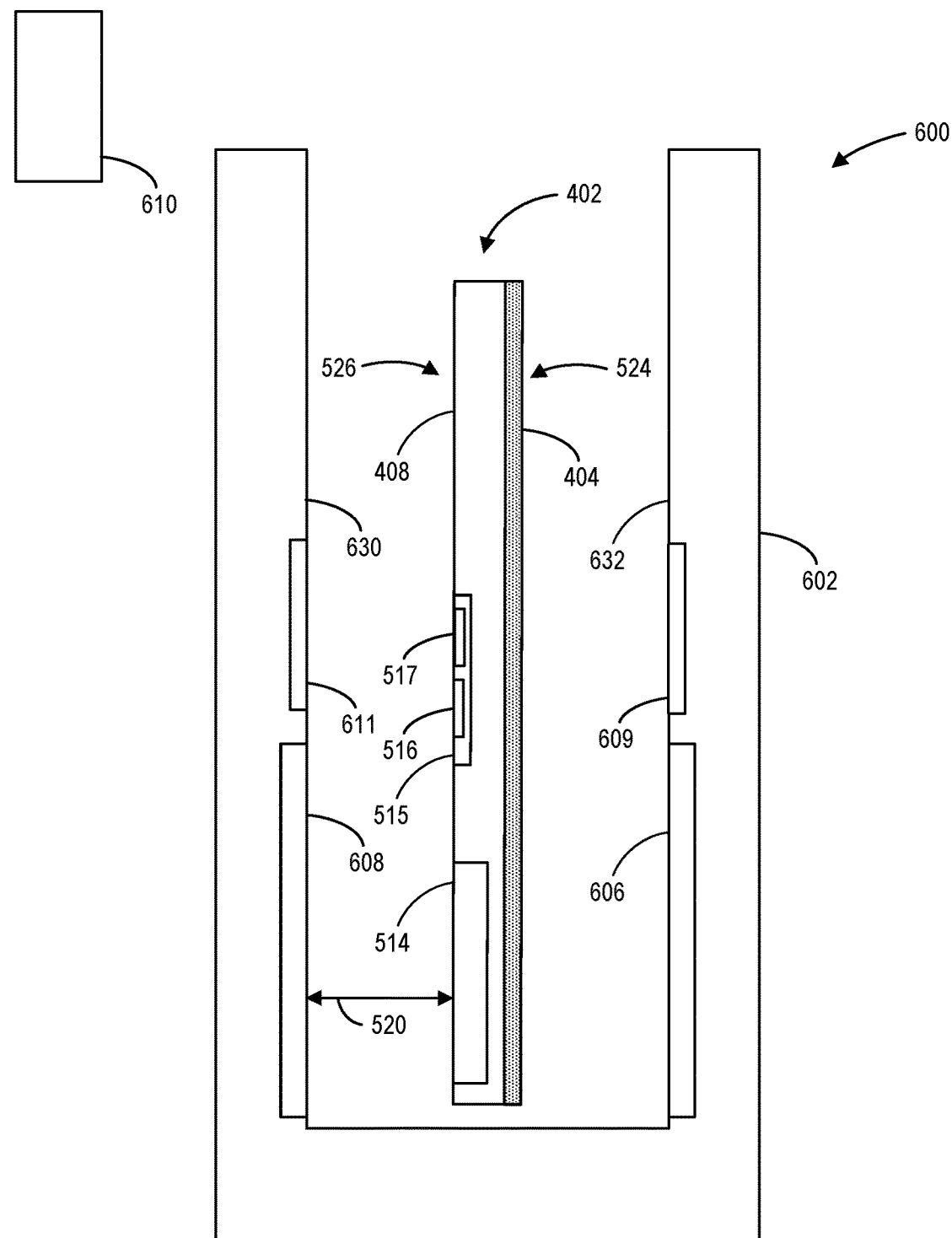
FIG. 6A shows a schematic view of a digital x-ray detector stored with a first orientation.
Figure 6B:
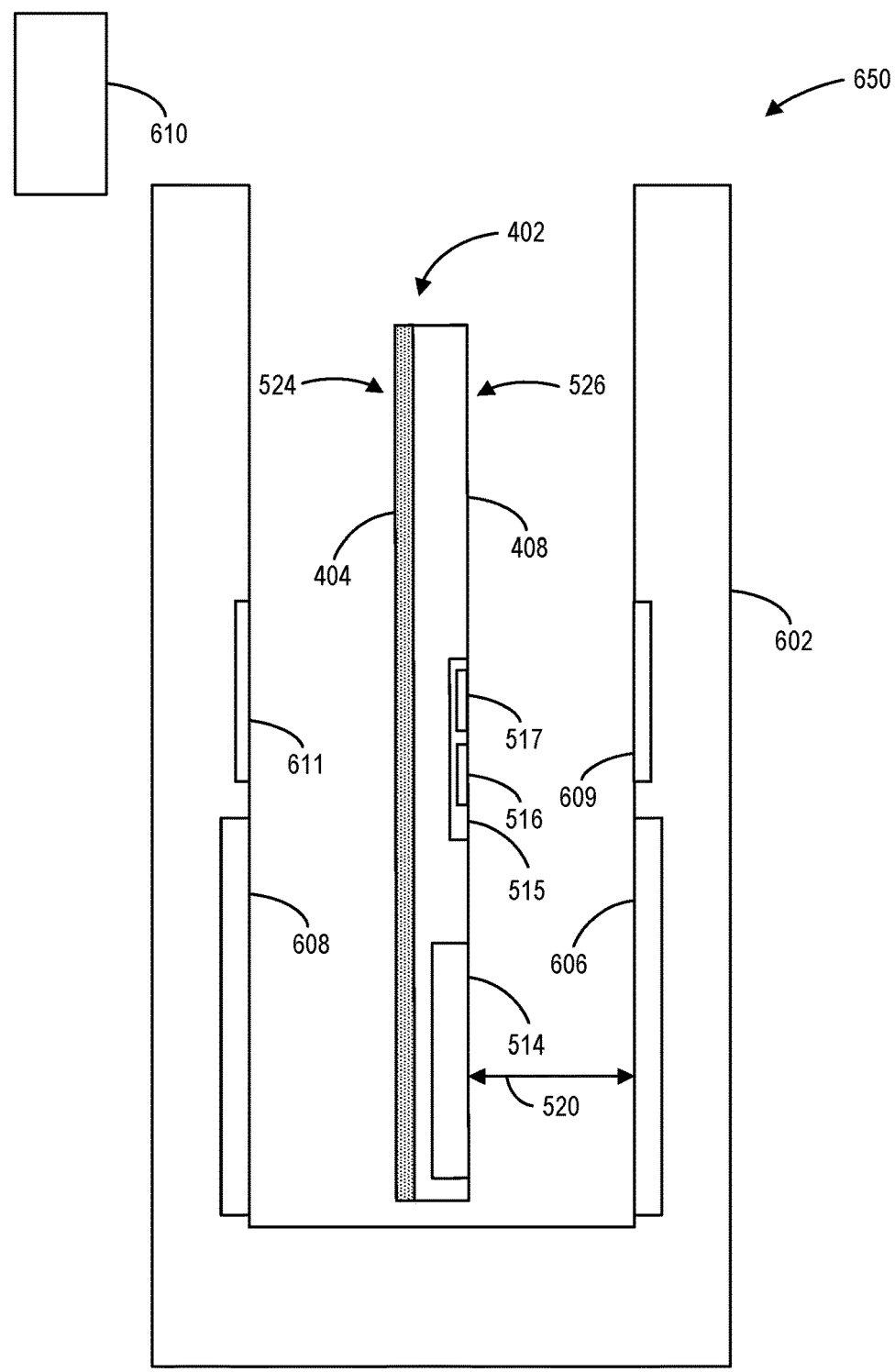
FIG. 6B shows a schematic view of the digital x-ray detector stored with a second orientation.
Figure 7:
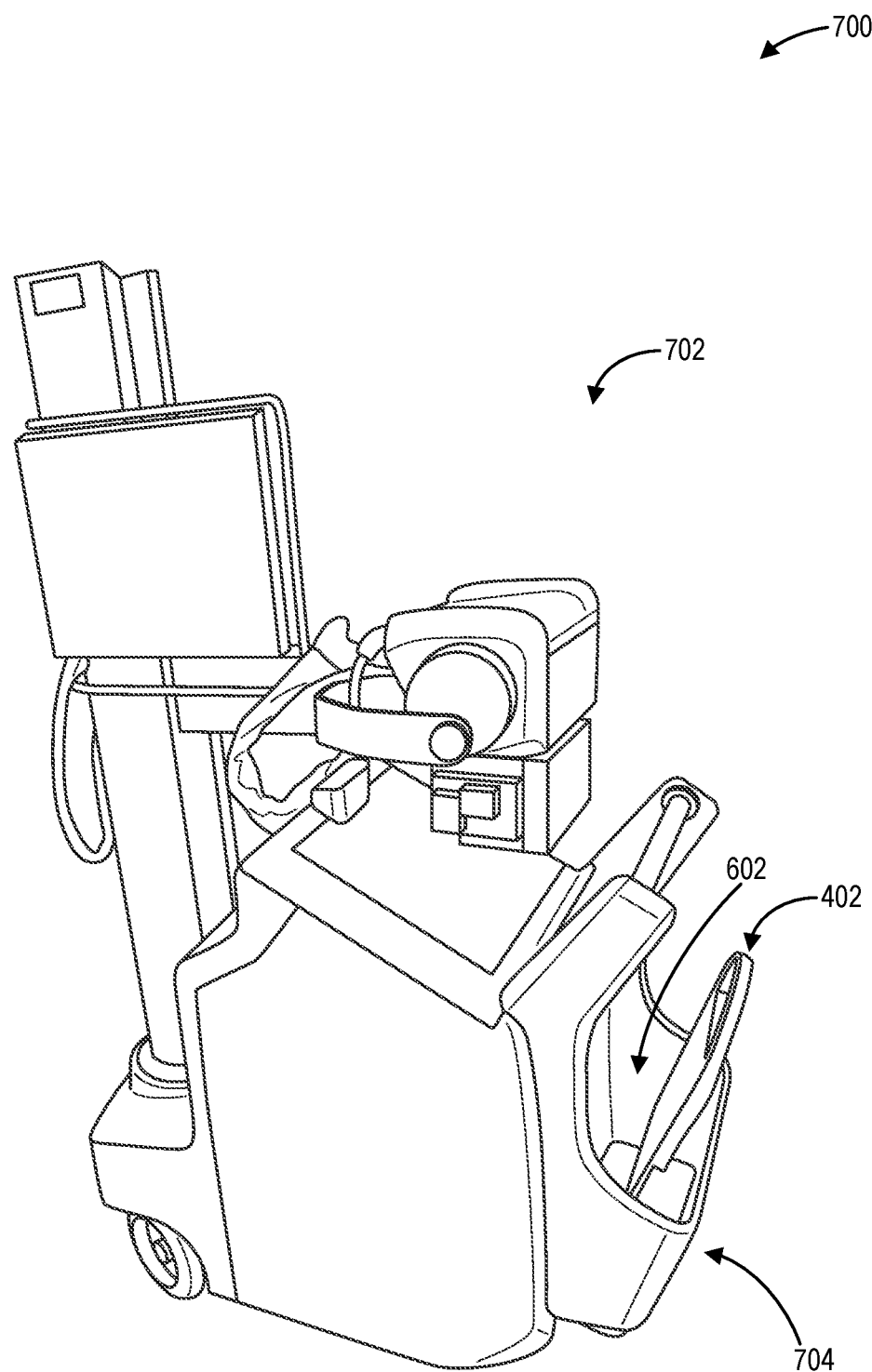
FIG. 7 shows a perspective view of a mobile x-ray system including a digital x-ray detector in a detector bin, according to an embodiment.
Figure 8:
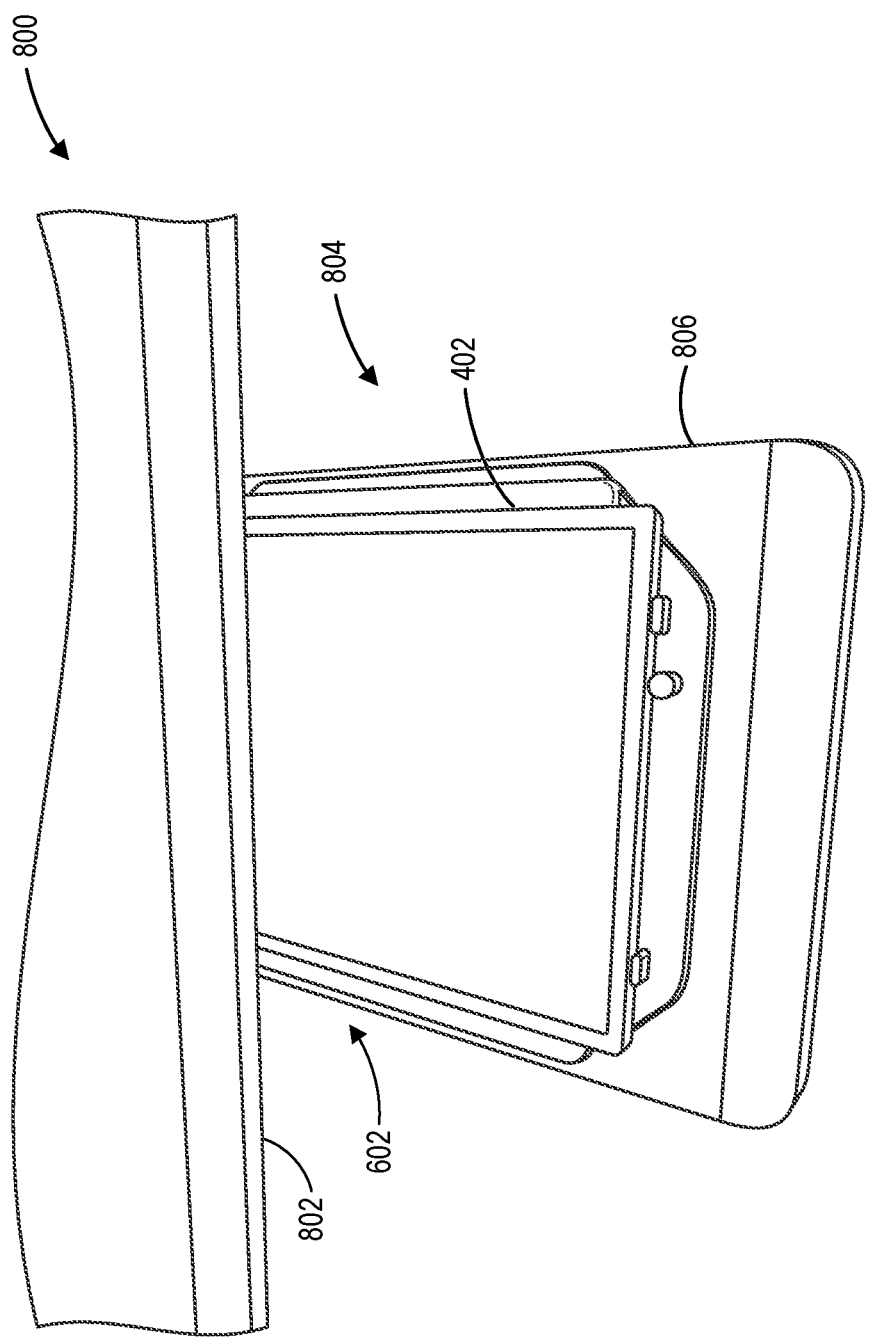
FIG. 8 shows a perspective view of a digital x-ray detector in a table drawer.
Figure 9:
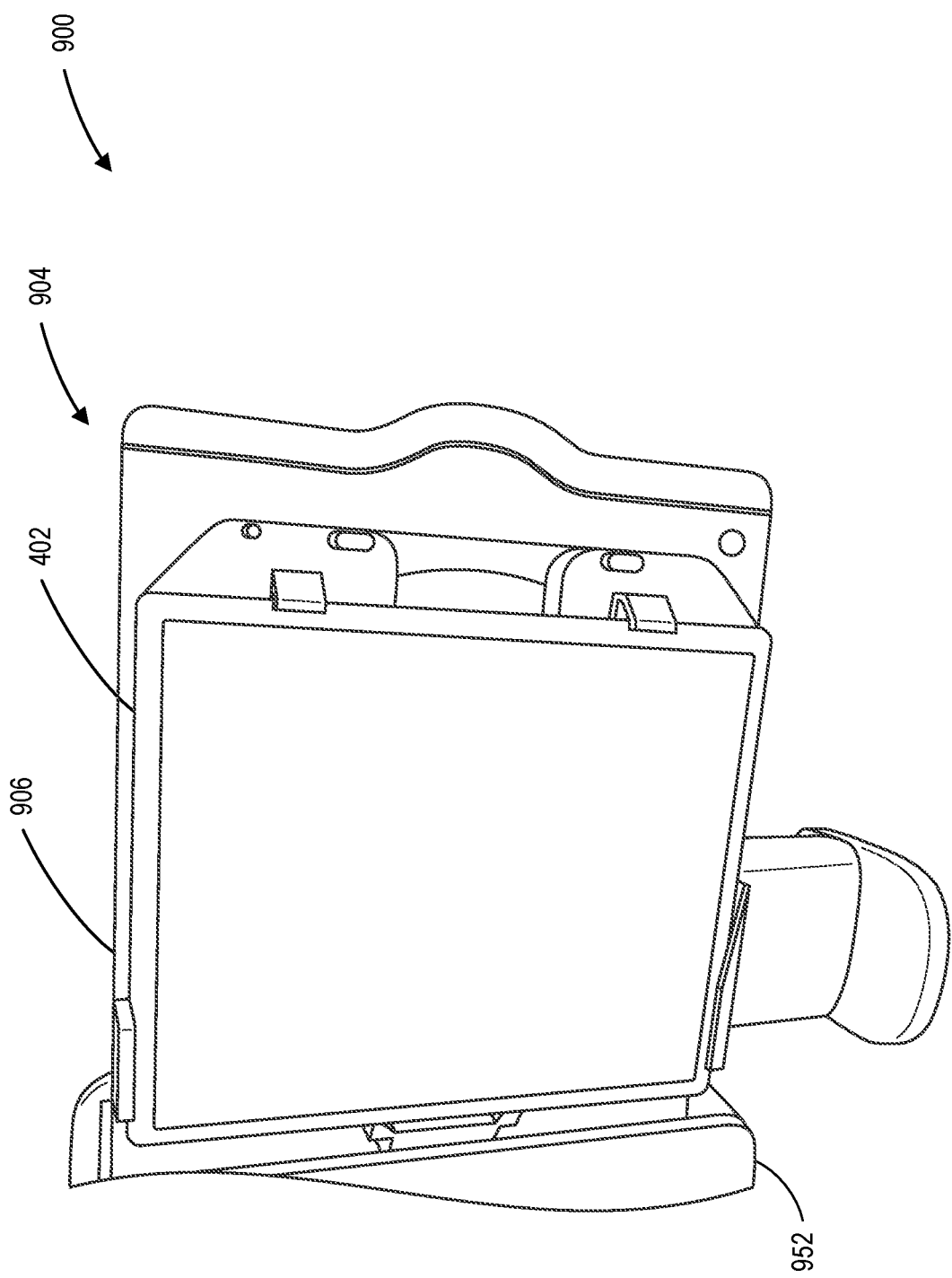
FIG. 9 shows a perspective view of a digital x-ray detector in a wallstand holder.
Figure 10:
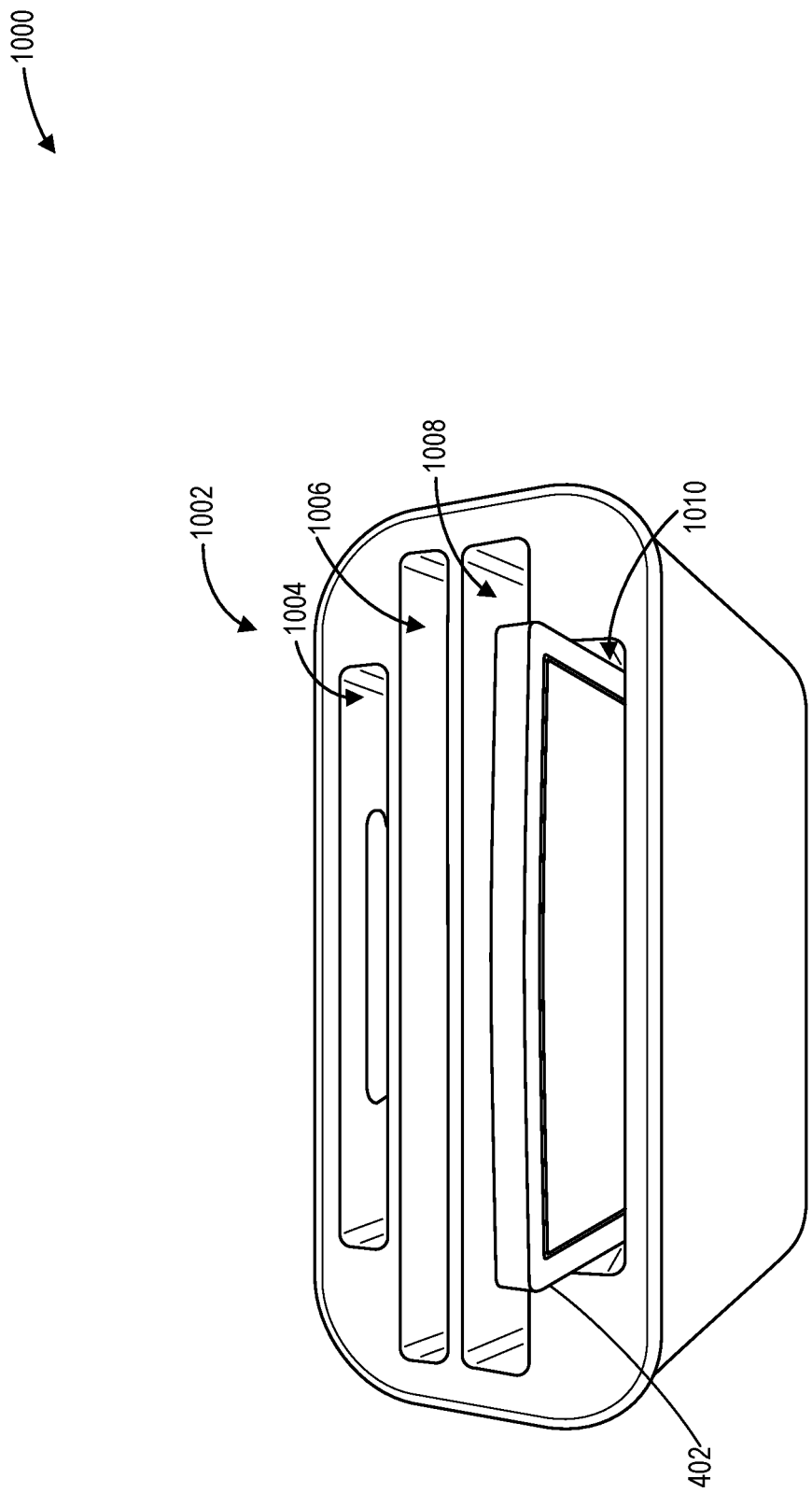
FIG. 10 shows a perspective view of a digital x-ray detector in a detector bin.

The following description relates to various embodiments of portable imaging systems. In particular, systems and methods are provided for authenticating and wirelessly charging a digital x-ray detector of an x-ray imaging system. A portable imaging system, such as the portable x-ray imaging system depicted in FIGS. 1 and 2, may include a digital x-ray detector powered by a rechargeable power supply, such as a battery or an internal capacitor. Further, FIG. 3 shows a stationary x-ray imaging system according to an embodiment of the present disclosure, which may include at least one digital x-ray detector powered by a rechargeable power supply. The digital x-ray detector included in the imaging systems of FIGS. 1 and 3 is shown in FIGS. 4A-5. In particular, FIG. 4A shows a front view of the digital x-ray detector, FIG. 4B shows a back view of the digital x-ray detector, and FIG. 5 shows an example cross-sectional view. The digital x-ray detector may be wirelessly charged via a wireless power connection placed in a charging area, such as in a first orientation shown in FIG. 6A and a second orientation shown in FIG. 6B. Next, FIG. 7 shows an example mobile x-ray imaging system including a detector bin including a charging area, while FIG. 8 shows a first example stationary imaging system including a detector drawer with a charging area, and FIG. 9 shows a second example stationary imaging system including a detector drawer with a charging area. FIG. 10 shows an embodiment of a detector bin including a charging area for charging a digital x-ray detector. For example, when the digital x-ray detector is placed in a charging area of an x-ray imaging system, the x-ray imaging system may establish a wireless network connection and a wireless power connection with the digital x-ray detector according to the method of FIG. 11. For example, the digital x-ray detector may be paired to the x-ray imaging system, and may be wirelessly charged. Further, before pairing, the x-ray imaging system may authenticate and register the digital x-ray detector according to the method of FIG. 12.

Advantages that may be realized in the practice of some embodiments of the described systems and techniques are that a digital x-ray detector may be wirelessly charged (e.g., charged without a connector) in a charging area of an x-ray imaging system, and may be paired with the x-ray imaging system in order to transmit medical imaging data to the x-ray imaging system. For example, decreasing a number of connectors of the x-ray imaging system may reduce a cost and complexity of the x-ray imaging system. Further, by authenticating and pairing the digital x-ray detector in the charging area, a secure connection between the digital x-ray detector and the x-ray imaging system may be established, allowing secure and efficient collection of medical imaging data from a patient.

Referring generally to FIG. 1, an x-ray imaging system (e.g., an x-ray system) is represented, referenced generally by reference numeral 12. In the illustrated embodiment, the x-ray system 12 may be a mobile digital x-ray system. The x-ray system 12 is designed both to acquire original images or image data and to process the image data for display (in a digital x-ray system). In particular, x-ray imaging system 12 may be substantially mobile, such that x-ray imaging system 12 may be moved between at least two distinct locations without any additional installation. Further, x-ray imaging system 12 may collect medical imaging data from a patient via a digital x-ray detector Thus, in the embodiment illustrated in FIG. 1, a view 10 is shown of an x-ray imaging system 12, which is a mobile digital x-ray system, and several accessories for operating the x-ray imaging system. Specifically, the imaging system 12 comprises a mobile imaging system that may be moved to a patient recovery room, an emergency room, a surgical room, or any other space to enable imaging of a patient 20 without requiring transport of the patient 20 to a dedicated (e.g., fixed) x-ray imaging room. The x-ray imaging system 12 includes a mobile x-ray base station 50 and a digital x-ray detector 22. In one embodiment, a support arm 52 may be vertically moved along a support column 54 to facilitate positioning of a radiation source 16 (also referred to herein interchangeably as x-ray tube 16) and a collimator 18 with respect to the patient 20 and the digital x-ray detector 22.

Further, one or both of the support arm 52 and support column 54 may also be configured to allow rotation of the radiation source 16 about an axis. The x-ray base station 50 may also include camera 24 to assist in positioning of the radiation source 16 and collimator 18, as well as speaker 44 to transmit patient-audible commands. The patient may be located on a bed 60 (or gurney, table, or any other support) between the radiation source 16 and the digital x-ray detector 22. During an imaging sequence using the digital x-ray system 10, the digital x-ray detector 22, also referred to herein as detector 22, receives x-rays that pass through the patient 20 and transmits imaging data to the base station 50. The digital x-ray detector 22 is in communication with the base station 50 via a wireless network connection. It is noted that the x-ray imaging system 12 and digital x-ray detector 22 may utilize any suitable wireless communication protocol, such as an Institute of Electrical and Electronics Engineers (IEEE) 802.15.4 protocol, an ultra-wideband (UWB) communication standard, a Bluetooth communication standard, or any IEEE 802.11 communication standard. As another example, the x-ray imaging system 12 and digital x-ray detector 22 may utilize Near-Field Communication (NFC) for communication. The base station 50 houses systems electronic circuitry 62 that acquires medical imaging data from the detector 22 and that processes the medical imaging data to form desired images, at least in some embodiments. In addition, the systems electronic circuitry 62 both provides and controls power to the radiation source 16 and the wheeled base 58 in the x-ray imaging system 12. As an example, the x-ray imaging system 12 and the digital x-ray detector 22 may communicate via a short-range protocol such as NFC or Bluetooth during a pairing process. For example, during the pairing process, the x-ray imaging system 12 may authenticate the digital x-ray detector 22, and enable the digital x-ray detector 22 to join a high-data, long-range network, such as a Wi-Fi network. As another example, the x-ray imaging system 12 and the digital x-ray detector 22 may communicate via the high-data, long-range network while acquiring and transferring medical imaging data.

Also depicted in FIG. 1, the x-ray imaging system 12 includes a workstation 32 and a display 34. More specifically, the base station 50 has the workstation 32 and display 34 that enables a user 36 to operate the x-ray imaging system 12. The operator workstation 32 may include buttons, switches, or the like to facilitate operation of the radiation source 16 and detector 22, for example. As another example, the operator workstation 32 may include a visual interface and a device for inputting text, such as a keyboard, a touchscreen, and the like. The x-ray base station 50 further includes a detector bin 64 for the digital x-ray detector 22 when detector 22 is not in use. The detector bin may be configured to recharge the battery of the detector 22. In particular, the bin 64 may be configured to recharge the battery of detector 22 via wireless (e.g., contactless) charging, as will be elaborated below.

In other embodiments, the functions of the x-ray imaging system 12 may be decentralized, such that some functions of the x-ray imaging system 12 are performed at the workstation 32, while other functions are performed by another component of the x-ray system 10, such as a handheld interface device (not shown). Further, some x-ray imaging systems may include a plurality of digital x-ray detectors. For example, a single x-ray system may include a first digital x-ray detector (e.g., a primary detector) and a second digital x-ray detector (e.g., a secondary detector). For example, the primary detector may be controlled differently than the secondary detector. In particular, the primary detector may be used for acquiring medical imaging data, while the secondary detector may not be used for acquiring medical imaging data. For example, by designating a primary detector, the user may control which detector of a plurality of detectors collects medical imaging data.

Figure 2:
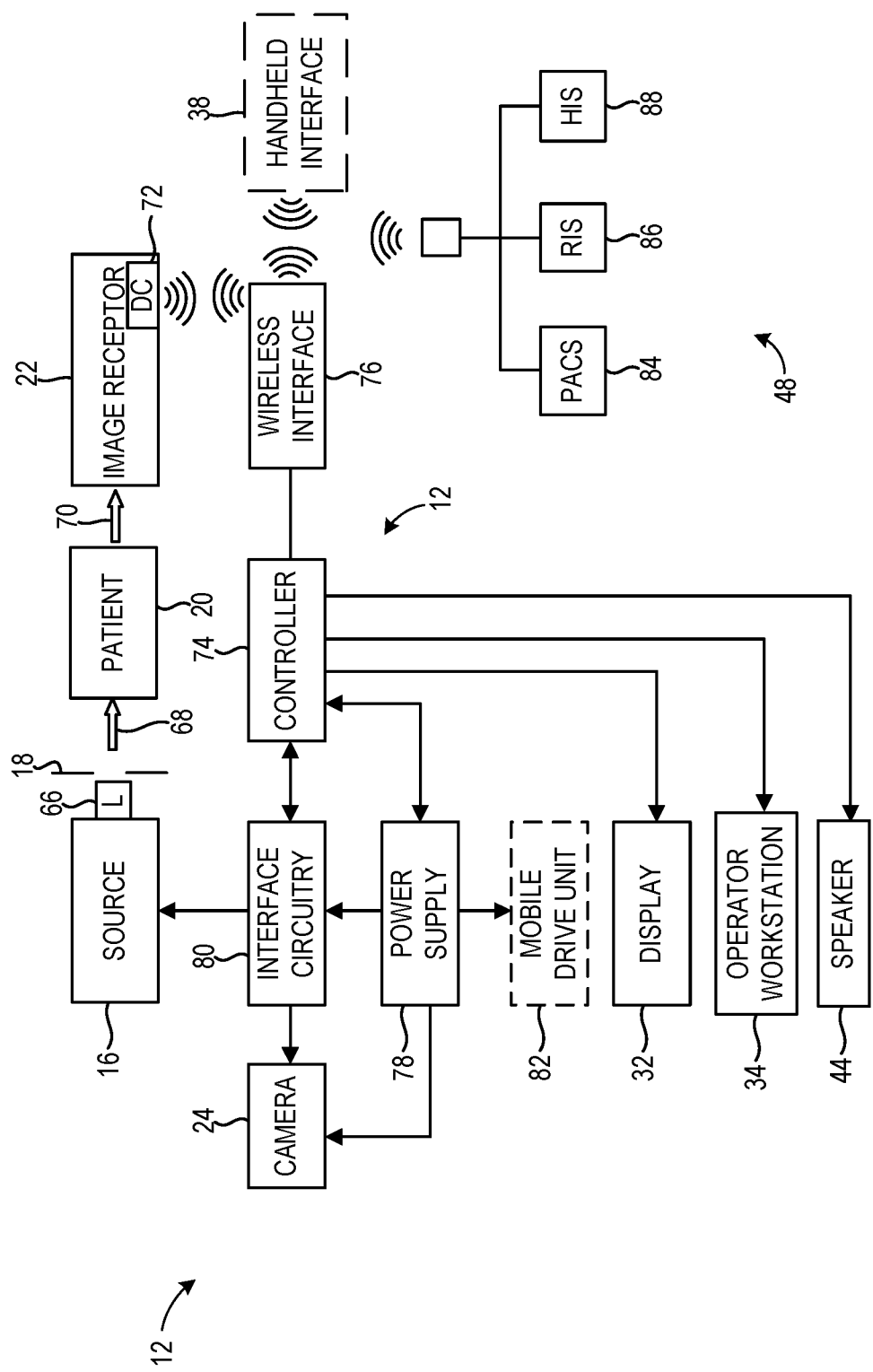
FIG. 2 shows a diagrammatical overview of the mobile x-ray system of FIG. 1.

FIG. 2 illustrates diagrammatically the x-ray imaging system 12 and digital x-ray detector 22 described in FIG. 1. As illustrated in FIG. 2, the x-ray system 12 includes the radiation source 16 positioned adjacent to the collimator 18. A light source 66, also known as a collimator light, is positioned between the radiation source 16 and the collimator 18. The collimator 18 permits a stream of radiation 68 or light to be directed to a specific region in which an object or subject, such as the patient 20, is positioned. A portion 70 of the radiation passes through the subject and impacts the image receptor or digital x-ray detector 22. As will be appreciated by those skilled in the art, the digital x-ray detector 22 converts the x-ray photons received on its surface to lower energy photons, and subsequently to electric signals, which are acquired and processed to reconstruct an image of the features within the subject. The collimator light 66 in the collimator 18 directs light onto the same area where the x-ray photons will pass and can be used to position the patient 20 before exposure. The collimator light 66 can be turned on and off with a user input on the x-ray imaging system 12 or on the handheld interface device 38.

Moreover, the digital x-ray detector 22 includes a detector controller 72 which commands acquisition of the signals generated in the detector 22. The detector controller 72 may also execute various signal processing and filtration functions, such as for initial adjustment of dynamic ranges, interleaving of digital image data, and so forth. For example, detector controller 72 includes a wireless communication module for wirelessly communicating with the x-ray imaging system 12. The detector controller 72 is operated responsive to signals from a controller 74 communicated wirelessly via a wireless interface 76. In general, the controller 74 commands operation of the x-ray imaging system 12 to execute examination protocols and to process acquired image data. In the present context, the controller 74 also includes signal processing circuitry, such as a programmed general purpose or application-specific digital computer, and associated devices. The associated devices may include optical memory devices, magnetic memory devices, or solid-state memory devices, for storing programs and routines executed by a processor of the computer to carry out various functionalities, as well as for storing configuration parameters and image data; interface circuits; and so forth.

In x-ray imaging system 12, the radiation source 16 is controlled by the controller 74, which controls signals for examination sequences. For example, the controller 74 can inhibit the operation of the radiation source 16 if the correct examination conditions are not in place. In addition, the controller 74 controls a power supply 78 that supplies power to the radiation source 16, light source 66, camera 24, and the controller 74. An interface circuitry 80 facilitates the provision of power to the radiation source 16, light source 66, camera 24, and controller 74. The power supply 78 also provides power to a mobile drive unit 82 to drive the movement of the wheeled base 58 of the x-ray base station 50. The power supply 78 may comprise one or more batteries. For example, the power supply 78 may comprise one or more lead-acid batteries.

The controller 74 is linked to at least one output device, such as display 32 or operator workstation 34. The output device may include standard or special purpose computer monitors and associated processing circuitry. One or more operator workstations 34 may be further linked in the system for outputting system parameters, requesting examinations, viewing images, and so forth. In general, displays, printers, workstations, and similar devices supplied within the system may be local to the imaging components or may be remote from these components, such as elsewhere within an institution or hospital or in an entirely different location. The displays, printers, workstations, etc. may be linked to the x-ray imaging system 12 via one or more configurable networks, such as the Internet, virtual private networks, and so forth. The controller 74 may also be linked to the speaker 44.

Further, the x-ray imaging system 12 optionally communicates wirelessly with a handheld interface device 38 via a wireless interface 76. For example, the operator may input control signals for the x-ray imaging system via the handheld interface device 38. The controller 74 provides the handheld interface device 38 system operational data (e.g., inhibit the operation of radiation source), images reconstructed from image data from the detector 22, images of the patient generated by the camera 24, patient data, and other information. For example, the handheld interface device 38 wirelessly communicates a signal to prepare for and initiate an exposure and other commands for operation of the x-ray imaging system 12, as well as the location and/or movement of the handheld interface device 38 relative to the system 12. Besides receiving patient data and/or instructions from the x-ray imaging system 12, the handheld interface device 38 wirelessly receives patient information and/or instructions (e.g., imaging sequences to be performed) from the medical facility's network 48. The medical facility network 48 includes a PACS 84, a RIS 86, and/or a HIS 88 to provide the information and/or instructions. The network 48 may also communicate the patient information and/or instructions to x-ray imaging system 12, which may then provide the information and/or instructions to the handheld interface device 38. In some examples, the handheld interface device 38 may not be included, and the operator workstation 34 may be used to control the above aspects of the imaging process.

Although a portable (e.g., mobile) imaging system is depicted in FIGS. 1 and 2, it should be appreciated that in some examples, an x-ray imaging system may be a stationary system disposed in a clinical environment. Turning now to FIG. 3, an example view of a stationary x-ray imaging system 300 is shown. In particular, stationary x-ray imaging system 300 includes an imaging system 302, a table 304, a vertical wallstand 306, and a digital x-ray detector 314. Digital x-ray detector 314 may be substantially identical to digital x-ray detector 22, described above in FIGS. 1 and 2. The table 304 includes a table surface 310, a detector drawer 308 for storing digital x-ray detector 314, and a base 312. In particular, detector drawer 308 may secure the digital x-ray detector 314 in order to perform imaging through table surface 310. For example, a patient may be positioned on the table surface 310 in a reclined position, so that a body part of the patient is directly above the digital x-ray detector 314 in the detector drawer 308. Table surface 310 may be translated vertically with respect to base 312 in order to adjust a position of a patient, for example. Similar to the mobile x-ray imaging system of FIG. 1, imaging system 302 may include a radiation source, a collimator, and a light source. Further, imaging system 302 may be coupled to a translation mechanism 316 to position imaging system 302 at multiple points throughout the room, such as over the table 304 and adjacent to the vertical wallstand 306. For example, imaging system 302 may be translated along a first axis 318 and a second axis 320 via translation mechanism 318, the first axis 318 perpendicular to the second axis 320.

As described above, both mobile x-ray imaging systems and stationary x-ray imaging systems may include digital x-ray detectors, such as digital x-ray detector 22 of FIG. 1 and digital x-ray detector 314 of FIG. 2. However, to maintain a charge of a rechargeable battery, existing digital x-ray detectors may be charged via a wired connection, which may decrease system flexibility while increasing a cost and complexity of the system. Further, during wired charging, a digital x-ray detector may be constrained to a single charging orientation due to connector design. As another example, charging ports may accumulate particulate matter during the course of operation, and may be difficult to clean. The inventors herein have advantageously realized the benefit of providing wireless charging to digital x-ray detectors in at least two orientations. Therefore, FIGS. 4A and 4B shows two example views of a digital x-ray detector 402 configured for wireless charging, which may be digital x-ray detector 22 of FIG. 1 or the digital x-ray detector 314 of FIG. 3, for example. Further, reference axes 499 are included in each of FIGS. 4A and 4B in order to compare the views and relative orientations described below. As shown in FIG. 4A and FIG. 4B, digital x-ray detector 402 may be bisected by a longitudinal axis 498. Longitudinal axis 498 is parallel to the y-axis of reference axes 499.

FIG. 4A shows a front view 400 of digital x-ray detector 402. The view 400 shown in FIG. 4A is an x-y planar view, as shown by reference axes 499. Digital x-ray detector 402 includes a detector front 404, as shown in FIG. 4A. The detector front 404 may allow x-ray radiation to interact with a detector array of digital x-ray detector 402 in order to produce x-ray images, as elaborated in FIG. 5.

FIG. 4B shows a back view 450 of x-ray detector 402. The view 450 shown in FIG. 4B is an x-y planar view, as shown by reference axes 499. However, back view 450 is rotated 180 degrees relative to front view 400 of FIG. 4A. As shown in back view 450, digital x-ray detector 402 includes a back panel 408, which may encase electronic components of digital x-ray detector 402. For example, back panel 408 may encase a battery and a wireless communication module of digital x-ray detector 402, which may provide digital x-ray detector 402 with a wireless network connection and a wireless power connection, as elaborated below in FIG. 5.

Next, FIG. 5 shows a schematic cross-sectional view 500 of digital x-ray detector 402 introduced above with respect to FIGS. 4A and 4B. Components of digital x-ray detector 402 previously introduced with reference to FIGS. 4A and 4B are numbered the same and may not be reintroduced. In particular, view 500 is a cross-sectional view of digital x-ray detector 402 in the x-z plane that highlights internal components of digital x-ray detector 402. As shown in FIG. 5, digital x-ray detector includes detector front 404, through which x-ray radiation may pass. For example, during an imaging procedure, x-ray radiation may pass through a patient and reach detector front 404, the x-ray radiation at least partially parallel to the z-axis of reference axis 499. As shown, detector front 404 is coupled to an external surface of digital x-ray detector 402, and a foam barrier 506 is directly below detector front 404 with respect to the z axes of references axis 499. For example, x-ray radiation directed at the digital x-ray detector 402 may pass through detector front 404 and the foam barrier 506 before reaching a scintillator 508, the scintillator directly below foam barrier 506 with respect to the z axes. Thus, as shown, each of the detector front 404, the foam barrier 506, and the scintillator 508 may be substantially parallel with respect to the x-y plane, as shown by references axis 499. For example, scintillator 508 may absorb energy from the x-ray radiation and re-emit the energy in the form of light (e.g., visible electromagnetic radiation). The light produced by scintillator 508 may be detected by a detector array 510, and may be used to produce a medical image of the patient. Further, digital x-ray detector 402 may include a stiffener 512, substantially parallel to detector front 404 that provides additional structural stability to the detector array 510.

Digital x-ray detector 402 includes the controller 515, which may be communicatively coupled to a long-range communication module 516 for communicating imaging data to an imaging system (e.g., such as x-ray imaging system 12 of FIG. 1 or imaging system 300 of FIG. 3), and a short-range communication module 517 for pairing with the imaging system via a short-range, low data rate connection. Controller 515 may be used similarly to detector controller 72 of FIG. 2, in some examples. For example, controller 515 may be communicatively coupled to at least one external computing system via a wireless network connection established by the long-range communication module 516. For example, a controller 515 may receive imaging data from detector array 510 via a wired connection 528 and may transmit data via the wireless network connection (e.g., such as Wi-Fi) to an x-ray imaging system (e.g., such as x-ray imaging system 10 of FIG. 1) or a computer. Further, during a pairing process, controller 515 may be communicatively coupled to at least one external computing system via a short-range connection such as NFC, Bluetooth, and the like, established by the short-range communication module 517. As one example, the short-range communication module 517 may establish an NFC connection during a pairing process, and the long-range communication module 516 may establish a Wi-Fi connection in order to transfer imaging data to the x-ray imaging system.

Further, controller 515, along with other components of digital x-ray detector 402, may receive power from a rechargeable power source 514. Rechargeable power source 514 may be selectively charged by a wireless power source 522 via a wireless power connection 520. For example, when digital x-ray detector 402 is placed in a charging area of an x-ray system (e.g., a detector bin, a detector drawer, and the like), rechargeable power source 514 may be charged (e.g., an amount of stored charge of rechargeable power source 514 may be increased) via the wireless power connection 520 with the wireless power source 522, such as an induction coil for producing wireless power, as will be elaborated below in FIGS. 6A and 6B. For example, the wireless power connection 520 may be an inductive charging connection between battery 514 and wireless power source 522. Both controller 515 and rechargeable power source 514 may be mechanically coupled to a circuit board 518. Further, in some embodiments, controller 515 and rechargeable power source 514 may be combined in a single component. For example, a single component may include controller 515 and rechargeable power source 514, so that wireless power and wireless communication are provided via the single component. Further, as shown in FIG. 5, the internal structural of digital x-ray detector 402 is asymmetrical. In particular, a front side 524 of digital x-ray detector 402 includes the detector front 404, while a back side 526 does not include a screen. Further, the scintillator 508, detector array 510, and stiffener 512 may block wireless power connection 520 from reaching rechargeable power source 514 from above along the z-axis (e.g., through front side 524). Thus, the back side 526 may be placed proximate to wireless power source 522 in order for rechargeable power source 514 to charge via the wireless power connection 520.

Note that FIG. 5 depicts one exemplary embodiment of a digital x-ray detector, and other embodiments may include more, fewer, or different components. As such, the description of FIG. 5 is not intended as an exhaustive list of components. In some embodiments of the present disclosure, the digital x-ray detector may include additional components in order to produce medical images and transmit data (e.g., including medical images) to a controller.

According to an embodiment of the present disclosure, a detector may be wirelessly charged in a charging area of an x-ray imaging system in at least two orientations. In order to better demonstrate the multiple charging orientations elaborated above, FIGS. 6A and 6B show schematic example views of a first orientation for wirelessly charging a digital x-ray detector in a charging area and a second orientation for wirelessly charging the digital x-ray detector in the charging area, respectively. In particular, FIGS. 6A and 6B show a digital x-ray detector 402 of FIGS. 4A and 4B, for example. Components of digital x-ray detector 402 will be numbered the same and not reintroduced. Further, the charging area 602 may be included in a detector storage area of an x-ray imaging system, as will be elaborated below in FIGS. 7-10. Further, reference axes 499 (e.g., of FIGS. 4 and 5) are included in each of FIGS. 6A and 6B in order to further compare the views and relative orientations described below. Internal components of digital x-ray detector 402 and charging area 602 are shown for reference, but may not be to scale. However, each of digital x-ray detector 402 and charging area 602 may include additional internal components not shown in FIGS. 6A and 6B.

First, FIG. 6A shows a schematic cross-sectional view 600 of the first orientation for wirelessly charging the digital x-ray detector 402 in the charging area 602, which may be included in an x-ray imaging system (such as x-ray imaging system 12 of FIGS. 1-2). In particular, view 600 of FIG. 6A is a z-y planar view of digital x-ray detector 402 in charging area 602, as shown by reference axes 499, in the first orientation. Charging area 602 may be included in a bin, slot, or drawer for storing digital x-ray detector 402, for example. As shown, charging area 602 includes a first side wall 630 and a second side wall 632, which may at least partially enclose digital x-ray detector 402. A long-range communication module 610 may be coupled directly to the charging area 602, or may be remote from the charging area 602, as shown in FIG. 6A. The long-range communication module 610 may establish a long-range, wireless network connection with digital x-ray detector 402 after a pairing process. Further, first side wall 630 includes a first wireless power source 608, and may include a short-range communication module 611 for establishing a short-range, low data rate wireless connection with digital x-ray detector 402. In some examples, the short-range communication module 611 and the first wireless power source 608 may be combined in a single component. For example, a single physical module may provide rechargeable power and wireless communication to the digital x-ray detector 402. Further still, second side wall 632 includes a second wireless power source 606, and may include a short-range communication module 609 for establishing a short-range, low data rate wireless connection with digital x-ray detector 402. In some examples, the short-range communication module 609 and the second wireless power source 606 may be combined in a single component. For example, digital x-ray detector 402 in FIG. 6A is rotated 90 degrees about the y axis relative to the view of digital x-ray detector 402 in FIG. 4. Front side 524 of digital x-ray detector 402 includes detector front 404 and faces the second wireless power source 606. Further, back side 526 of digital x-ray detector 402 includes back panel 408 and faces the first wireless power source 608.

Further, as shown, rechargeable power source 514 of the digital x-ray detector is mechanically coupled to the back side 526, so that a wireless power connection 520 electrically couples rechargeable power source 514 and first wireless power source 608. Thus, in the first orientation, rechargeable power source 514 is oriented toward first wireless power source 608, without any other internal components of digital x-ray detector 402 positioned between rechargeable power source 514 and first wireless power source 608 (such as wireless power source 522 shown in FIG. 5). Further, in the first orientation, rechargeable power source 514 may be wirelessly charged by first wireless power source 608 via wireless power connection 520, but may not form a wireless power connection with a second wireless power source 606 and may not be charged by the second wireless power source 606. As an example, the internal components of digital x-ray detector 602 may physically prevent a wireless power connection (e.g. block or attenuate the wireless connection) between the second wireless power source 606 and the rechargeable power source 514 while digital x-ray detector 602 is in the first orientation shown in FIG. 6A.

In some examples, rechargeable power source 514 may be directly electrically coupled to first wireless power source 608. However, in other examples, the first wireless power source 608 may transmit power to a separate module physically separated from rechargeable power source 514.

As shown in FIG. 6A, digital x-ray detector 402 is communicatively coupled to the x-imaging system. For example, long-range communication module 516 of the digital x-ray detector 402 is communicatively coupled to long-range communication module 610 of the x-ray imaging system via a long-range wireless network connection (such as Wi-Fi, UWB, and the like). In some examples, the long-range communication module 610 of the x-ray imaging system may be located in a charging area, while in other examples the long-range communication module 610 may be remote from the charging area. Further, short-range communication module 517 of the digital x-ray detector 402 is communicatively coupled to at least one of short range communication module 609 and short-range communication module 611 of the x-ray imaging system via a short-range, low data rate connection (e.g., such as NFC, Bluetooth, and the like). The short-range communication module 611 and the short range communication module 609 of the x-ray imaging system is included in the charging area in order to enable the short-range data connection. For example, when digital x-ray detector 402 is placed in charging area 602 in the orientation shown in FIG. 6A, the short-range communication module 611 may establish a short-range pairing connection with short-range communication module 517 of the digital x-ray detector via a short-range, low data rate protocol such as NFC, Bluetooth, and the like. Further, the long-range communication module 610 may establish a long-range wireless connection with long-range communication module 516 to allow for the digital x-ray detector to access the long-range wireless network connection. For example, the long-range network connection may be used to transmit medical imaging data collected by the digital x-ray detector. Further, in some examples, establishing a wireless network connection with long-range communication module 516 of the digital x-ray detector may include authenticating and registering digital x-ray detector, and then pairing the detector to the x-ray imaging system (as elaborated below in FIGS. 10 and 11).

In the embodiment shown, the x-ray imaging system includes two short-range communication modules, short-range communication module 611 and a short-range communication module 609, each of the short-range communication module 611 and the short-range communication module 609 configured to connect to the short-range communication module 517 of the digital x-ray detector via a short-range, low data rate wireless connection. For example, short-range communication module 517 of the digital x-ray detector 402 may connect with the closer short-range communication module, so that in the first orientation of FIG. 6A, short-range communication module 517 is communicatively coupled to short-range communication module 611. Further, in some embodiments, the short-range communication module 611 may be combined with the first wireless power source 608 in a single component, and the short-range communication module 609 may be combined with the second wireless power source 606. Put differently, a single component of the x-ray imaging system, referred to as a combined power and short-range data module, may provide wireless power and a short-range wireless connection. In order to provide wireless power and the short-range wireless connection in at least two orientations, the charging area may include two combined power and short-range data modules.

Next, FIG. 6B shows a schematic cross-sectional view 650 of the second orientation for wirelessly charging the digital x-ray detector 402 in the charging area 604 of an x-ray imaging system (not shown). In particular, view 650 is a z-y cross-sectional view of digital x-ray detector 402 in charging area 602 in the second orientation. In particular, charging area 602 is in the same orientation as shown in FIG. 6A, while digital x-ray detector 402 is rotated 180 degrees about a central longitudinal axis, the central longitudinal axis parallel to the y-axis of reference axes 499. Thus, as shown in FIG. 6B, the front side 524 of digital x-ray detector 402 faces the first wireless power source 608. Further, the back side 526 of digital x-ray detector 402 faces the second wireless power source 606. As such, digital x-ray detector 402 is rotated 180 degrees about the y-axis in the second orientation relative to the first orientation (e.g., shown in FIG. 6A). Further, as shown, the rechargeable power source 514 of the digital x-ray detector is fixed to the back side 526, such that the wireless power connection 520 electrically couples rechargeable power source 514 and the second wireless power source 606. Further, as shown, in the second orientation, rechargeable power source 514 is oriented toward second wireless power source 606, without any other internal components of digital x-ray detector 402 positioned between rechargeable power source 514 and second wireless power source 606. For example, back side 526 is closer to the second wireless power source 606 than the first wireless power source 608 in the second orientation. Further, other internal components of digital x-ray detector 402 (e.g., such as scintillator 510 shown in FIG. 5) may attenuate (e.g., weaken or interrupt) a wireless power connection between rechargeable power source 514 and first wireless power source 608. As such, rechargeable power source 514 may be charged by the second wireless power source 606 via wireless power connection 520 in the second orientation and may not be charged by the first wireless power source 608 in the second orientation. Similarly, in the second orientation, short-range communication module 517 of the digital x-ray detector may establish a connection with short-range communication module 609 of the x-ray imaging system, and may not establish a connection with short-range communication module 611 of the x-ray imaging system.

In some examples, rechargeable power source 514 may be directly electrically coupled to second wireless power source 606. However, in other examples, the second wireless power source 606 may transmit power to a separate module physically separated from rechargeable power source 514.

In this way, a digital x-ray detector, such as digital x-ray detector 402, shown in FIGS. 4A and 4B, may be wirelessly charged via a wireless power connection with an x-ray imaging system in at least two orientations. Thus, a digital x-ray detector may be placed in a charging area of an x-ray imaging system, such as charging area 602 of FIGS. 6A and 6B, in order to be wirelessly charged. In some examples, the digital x-ray detector 402 may be charged in more than two orientations. For example, in addition to the first orientation and the second orientation shown in FIGS. 6A and 6B, the digital x-ray detector 402 in a third orientation may be rotated about the z-axis of reference axes 499. The charging area of the x-ray imaging system may be included in a storage area for digital x-ray detectors. For example, the x-ray imaging system may include at least one detector drawer, detector bin, detector shelf, detector slot, or other detector storage area for storing and wirelessly charging a digital x-ray detector. For example, when the digital x-ray detector is placed in a charging area, such as a detector bin, a detector drawer, and the like, the x-ray imaging system may provide wireless power to the digital x-ray detector without any connectors and/or cables. In order to illustrate example embodiments of storage areas for digital x-ray detectors including a charging area, FIGS. 7-10 show example storage areas for digital x-ray detectors including a charging area.

First, FIG. 7 shows a perspective view 700 of a mobile x-ray imaging system 702 including a detector bin 704. FIG. 7 may be similar to x-ray imaging system 12 of FIG. 1, and as such, may be used to collect medical imaging data via a digital x-ray detector. Further, detector bin 704 includes charging area 602, such as described above in FIGS. 6A and 6B. For example, detector bin 704 includes at least two wireless power sources for recharging a battery of a digital x-ray detector. Digital x-ray detector 402 is shown placed in detector bin 704 for storage and charging. Digital x-ray detector 402 is shown including an optional handle in FIG. 7. In some embodiments, digital x-ray detector 402 may not include a handle. Digital x-ray detector 402 may be substantially identical to the digital x-ray detector 402 shown in FIGS. 4A-6B. For example, when the digital x-ray detector 402 is not being used to collect medical imaging data, it may be stored in the detector bin 704, as shown in FIG. 7. For example, digital x-ray detector 402 is shown in a first orientation, and as such, may be wirelessly charged via a first wireless power source. Further, when stored in the detector bin 704, as shown, digital x-ray detector 402 may be paired to the mobile x-ray imaging system. Methods for pairing a digital x-ray detector to an imaging system are elaborated below in FIG. 6. In this way, a digital x-ray detector may be charged in a charging area of an x-ray imaging system.

Stationary x-ray imaging systems may also include at least one charging area for a digital x-ray detector. As such, FIG. 8 shows a view 800 of a detector drawer 804 of a stationary x-ray imaging system, such as stationary imaging system 300 shown in FIG. 3. For example, detector drawer 804 may be configured similar to detector drawer 308 of FIG. 3. Further, detector drawer 804 includes charging area 602, such as described above in FIGS. 6A and 6B. For example, detector drawer 804 includes at least two wireless power sources for recharging a rechargeable power source of a digital x-ray detector. For example, including at least two wireless power sources may enable charging in two detector orientations, such as a portrait orientation and a landscape orientation of a rectangular detector, such as the detector 402 shown in FIG. 4. For example, in each of the two orientations, the rechargeable power source may be offset, so that in a first orientation (e.g., the portrait orientation) the rechargeable power source is closer to a first wireless power source, and in a second orientation (e.g., the landscape orientation) the rechargeable power source is closer to a second wireless power source. In the view 800 of FIG. 8, a bottom shelf 806 of detector drawer 804 is extended to show digital x-ray detector 402 stored in the detector drawer 804. For example, detector drawer 804 may include a first wireless power source and a second wireless power source for wirelessly charging the digital x-ray detector.

As another example, FIG. 9 shows a view 900 of a detector drawer 904 of a stationary x-ray imaging system, such as stationary imaging system 300 shown in FIG. 3. Further, detector bin 904 includes charging area 602, such as described above in FIGS. 6A and 6B. For example, detector drawer 904 includes at least two wireless power sources for recharging a battery of a digital x-ray detector. In the view 900 of FIG. 9, the shelf 906 of detector drawer 904 is extended to show a digital x-ray detector 402 stored in the detector drawer (e.g., in the charging area 602). For example, detector drawer 904 may include a first wireless power source and a second wireless power source for wirelessly charging the digital x-ray detector, as described above with respect to FIGS. 6A and 6B. For example, including at least two wireless power sources may enable charging in two detector orientations, such as a portrait orientation and a landscape orientation of a rectangular detector, such as the detector 402 shown in FIG. 4. For example, in each of the two orientations, the rechargeable power source may be offset, so that in a first orientation (e.g., the portrait orientation) the rechargeable power source is closer to a first wireless power source, and in a second orientation (e.g., the landscape orientation) the rechargeable power source is closer to a second wireless power source.

Further, some x-ray imaging systems may include a free-standing detector bin for charging and storing digital x-ray detectors. A free-standing detector bin may be used with a plurality of mobile x-ray imaging systems or a with fixed x-ray imaging system. Therefore, FIG. 10 shows an example view 1000 of a detector bin 1002 for wirelessly charging and storing at least one digital x-ray detector. Detector bin 1002 includes a plurality of charging slots, including a first charging slot 1004, a second charging slot 1006, a third charging slot 1008, and a fourth charging slot 1010. For example, each of the charging slots may comprise a charging area, such as charging area 602 shown in FIGS. 6A and 6B. As such, a detector may be placed in each of the first charging slot 1004, the second charging slot 1006, the third charging slot 1008, and the fourth charging slot 1010 in order to be wirelessly charged. For example, each charging slot includes at least two wireless power sources for wirelessly charging a digital x-ray detector in at least two orientations. As shown in FIG. 10, detector bin 1002 includes digital x-ray detector 402 in fourth charging slot 1010.

In this way, a digital x-ray detector may be wirelessly charged when placed in a charging area of an x-ray imaging system. Further, when the digital x-ray detector is placed in the charging area, such as charging area 602 shown in FIGS. 6A and 6B, a controller of the x-ray imaging system may initiate a pairing process in order to establish a secure network connection with the detector. Pairing the digital x-ray detector to the x-ray imaging system links helps set up an initial linkage between the two devices to allow communications between them. In particular, a controller of the digital x-ray detector (such as controller 515 of digital x-ray detector 402 shown in FIG. 5) may be paired with a controller of the x-ray imaging system. For example, pairing the digital x-ray detector to the x-ray imaging system via a short-range, low data rate protocol (e.g., such as NFC or Bluetooth) may authenticate the digital x-ray detector and establish a secure high-speed network connection (e.g., such as Wi-Fi or UWB) and allow the x-ray imaging system to at least partially control the digital x-ray detector. As one example, when the digital x-ray detector is paired to the x-ray imaging system, the digital x-ray detector may be controlled to collect medical imaging data and transmit the medical imaging data to the x-ray imaging system. In some examples, pairing the digital x-ray detector to the x-ray imaging system includes a registration process for ensuring that a detector is authorized for use with an x-ray imaging system. Digital x-ray detectors, such as described in FIGS. 4A-5, may be used interchangeably among various stationary and mobile x-ray imaging systems within a clinical setting. For example, a first digital x-ray detector may be used with a first x-ray imaging system to collect medical imaging data from a first patient, and may then be used with a second x-ray imaging system to collect medical imaging data from a second patient. Such interchangeable use may facilitate patient care, and may increase a diagnostic speed within a clinical environment by enabling timely x-ray examination. For example, a single digital x-ray detector may be transferred between multiple x-ray imaging systems.

Figure 11:
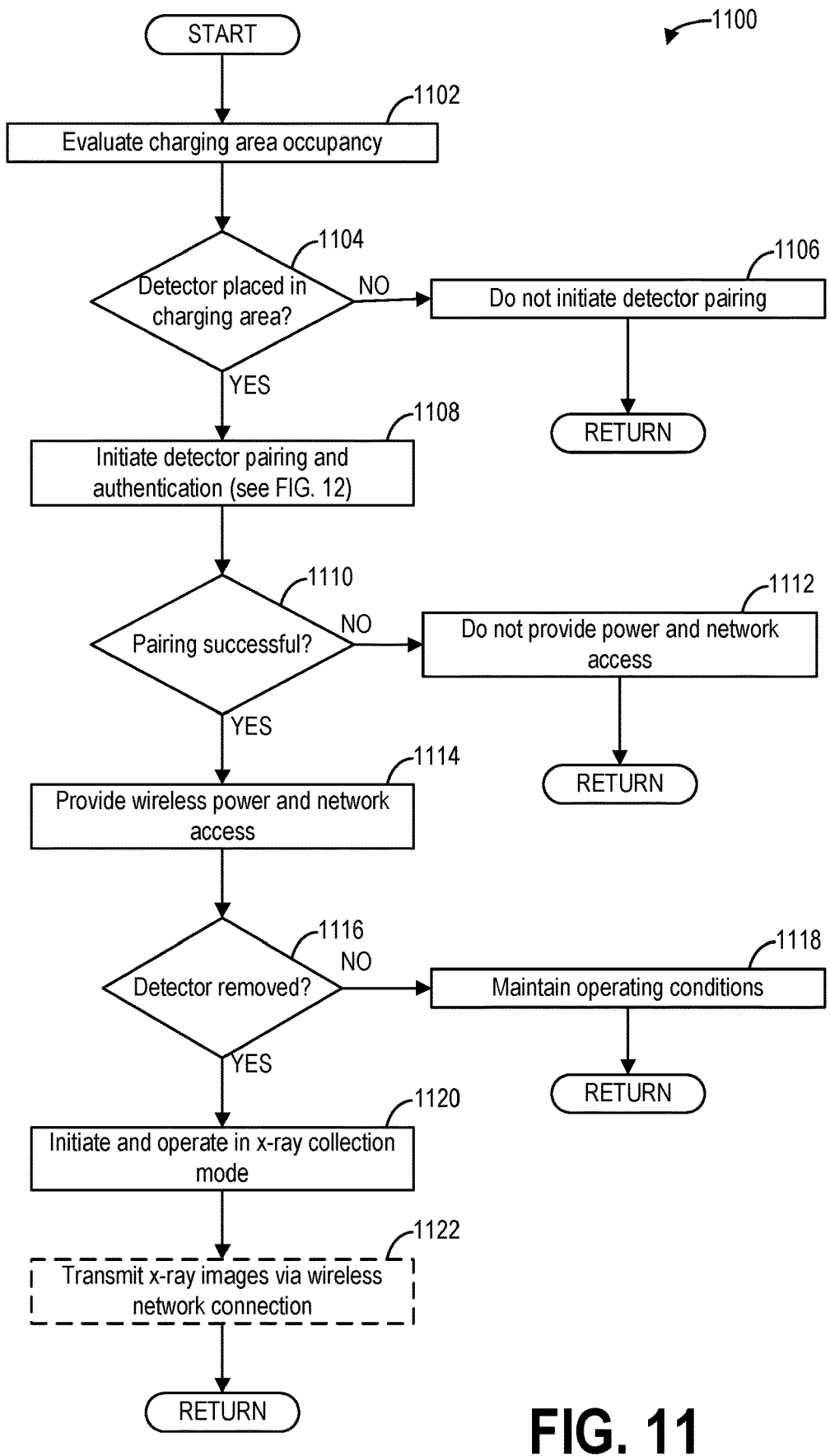
FIG. 11 shows a flowchart of a method for operating an x-ray imaging system to provide a wireless power connection and a wireless network connection to a digital x-ray detector with wireless charging.

Turning now to FIG. 11, a high-level flow chart of an example method 1100 for pairing a digital x-ray detector with an x-ray imaging system and wirelessly charging the digital x-ray detector in a charging area of the x-ray imaging system is shown. The x-ray imaging system may be a mobile x-ray imaging system or a stationary x-ray imaging system (e.g., such as mobile x-ray imaging system 12 of FIG. 1 or stationary x-ray imaging system 300 of FIG. 3), and may include a digital x-ray detector (e.g., as described with respect to FIGS. 4A-5). Method 1100 and the rest of the methods included herein may be executed by a controller, such as controller 74 of FIG. 2, according to instructions stored in a memory of the controller and in conjunction with one or more inputs, such as inputs received from an operator via an operator workstation (e.g., operator workstation 34 of FIG. 2) and one or more signals received from the digital x-ray detector. Further, the controller may output information to the operator of the x-ray imaging system via the operator workstation and/or a display.

At 1102, method 1100 includes evaluating a charging area occupancy. For example, to evaluate the charging area occupancy, the controller determines whether a digital x-ray detector, such as the digital x-ray detector described with respect to FIGS. 4A-5, is proximate to a charging area of the x-ray imaging system. The charging area may be one of a detector drawer and a detector bin, for example. As an example, evaluating the charging area occupancy may include monitoring an operator workstation for a user input and monitoring a charging area for a detector. For example, the charging area may include a pressure sensor, and may determine that the digital x-ray detector is in the charging area responsive to a signal from the pressure sensor indicating increased pressure. As another example, the controller may determine that the detector is placed on the charging area based on a short-range, low data rate wireless connection, such as NFC or Bluetooth. As another example, the controller may determine that the detector is placed on the charging area based on a connection between a power transmitting coil and a power receiving coil (e.g. of the digital x-ray detector) via a wireless charging protocol such as the Qi standard. For example, the controller may determine that the digital x-ray detector is in the charging area based on the NFC signal strength, such as when the NFC signal strength is greater than a threshold signal strength corresponding to the digital x-ray detector being within a pre-determined distance of the controller. As yet another example, a user may input a command to the controller via the operator workstation indicating that the digital x-ray detector is in the charging area.

At 1104, method 1100 includes determining whether the detector is in the charging area based on the charging area occupancy. If the controller determines that the detector is not placed in the charging area at 1104, method 1100 continues to 1106, and includes not initiating detector pairing and registration. Further, because no detector is in the charging area, wireless charging is not provided. Method 1100 may then return.

If the controller determines that the detector is placed in the charging area at 1104, method 1100 continues to 1108 and includes initiating detector pairing and registration. For example, the controller may pair the detector to the x-ray imaging system, in order to establish a secure network connection between the digital x-ray detector and the x-ray imaging system, such as a long-range, high-data network connection (e.g., such as Wi-Fi, UWB, and the like). As an example, the controller may authenticate the digital x-ray detector before pairing, such as is elaborated below with respect to FIG. 12.

At 1110, method 1100 includes determining whether the pairing process at 1108 was successful. For example, the controller may determine whether the digital x-ray detector was authenticated and paired to the x-ray imaging device. As an example, the pairing process may not be successful when the digital x-ray detector cannot be authenticated during the pairing process. As another example, the pairing process may not be successful when the digital x-ray detector is suddenly moved during pairing, or if the digital x-ray detector is damaged such that a secure network connection cannot be established.

If method 1100 determines that the pairing process was not successful at 1108, method 1100 continues to 1112 and includes not providing wireless power and network access to the digital x-ray detector. For example, the controller may not provide current to an induction coil in order to wirelessly charge the rechargeable battery of the digital x-ray detector, and the controller may not provide a secure network connection to the digital x-ray detector. Further, the controller may display an error message to the operator via a display coupled to the x-ray system, prompting the operator to address the unsuccessful pairing process. Method 1100 may then return.

If method 1100 determines that the pairing process was successful at 1108, method 1100 continues to 1114 and includes providing wireless power and network access. For example, providing wireless power includes establishing a wireless power connection between a power source of the charging area and a rechargeable battery of the digital x-ray detector and providing wireless power to the rechargeable battery via the wireless power connection. For example, the wireless power connection may be compliant with a Ki wireless charging standard, a Qi wireless charging standard, or any other wireless charging standard known in the art. For example, the power source of the charging area may comprise at least one induction coil that provides wireless charging to the rechargeable battery of the digital x-ray detector when a current is applied to the induction coil. Further, providing network access may include establishing a long-range, high-data wireless network connection between a wireless interface of the x-ray imaging system and a wireless interface of the digital x-ray detector. For example, the controller may establish a secure network connection via Wi-Fi, UWB, etc. For example, the long0range, high-data wireless network connection may be used to transfer medical imaging data from the digital x-ray detector to the x-ray imaging system.

At 1116, method 1100 includes determining whether the detector has been removed from the charging area. For example, the controller may determine that the digital x-ray detector has been removed from the charging area based on a signal from the pressure sensor, indicating decreased pressure in the charging area. As another example, the controller may determine that the digital x-ray detector has left the charging area based the strength of the network connection, such as a NFC connection. As yet another example, the controller may determine that the digital x-ray detector has been removed from the charging area based on an operator input via the operator workstation.

If the controller determines that the detector has not been removed from the charging area at 1116, method 1000 continues to 1118, and includes maintaining wireless power and network access. For example, maintaining operating conditions when the detector has not been removed from the charging area may include continuing to wirelessly charge the digital x-ray detector via the wireless power connection while maintaining a wireless network connection. Method 1100 then returns.

If the controller determines that the detector has been removed from the charging area at 1116, method 1100 continues to 1120 and includes initiating and operating in an x-ray collection mode. For example, initiating the x-ray collection mode may include instructing the digital x-ray detector to execute an x-ray collection program.

At 1122, method 1000 optionally includes transmitting x-ray images via the wireless network connection. For example, the digital x-ray detector may transmit medical imaging data collected while operating in the x-ray collection mode, via the wireless network connection. For example, a display of the x-ray imaging system may display at least one medical image transmitted by the digital x-ray detector. Additionally or alternatively, the medical imaging data transmitted by the digital x-ray detector may be stored in a memory of the controller and not displayed to the operator. After 1018, method 1000 may return. In some examples, method 1000 may run continuously on the controller of the digital x-ray detector.

In clinical settings, such as a hospital, a clinic, or a medical office, increased network security may increase customer satisfaction. For example, a customer may want to ensure that only pre-approved devices successfully register with an x-ray imaging system for collecting medical images via a secure network connection. For example, an x-ray imaging system operator may want to ensure that an unapproved digital x-ray detector does not collect medical images using the x-ray imaging system. Further still, the operator may want to prevent other devices from accessing the secure network connection. For example, an x-ray imaging system may issue an authentication challenge to a new digital x-ray detector, and may authenticate the detector (e.g., determine whether the detector is approved) before registering the detector with the x-ray imaging system for producing and transmitting medical imaging data.

Figure 12:
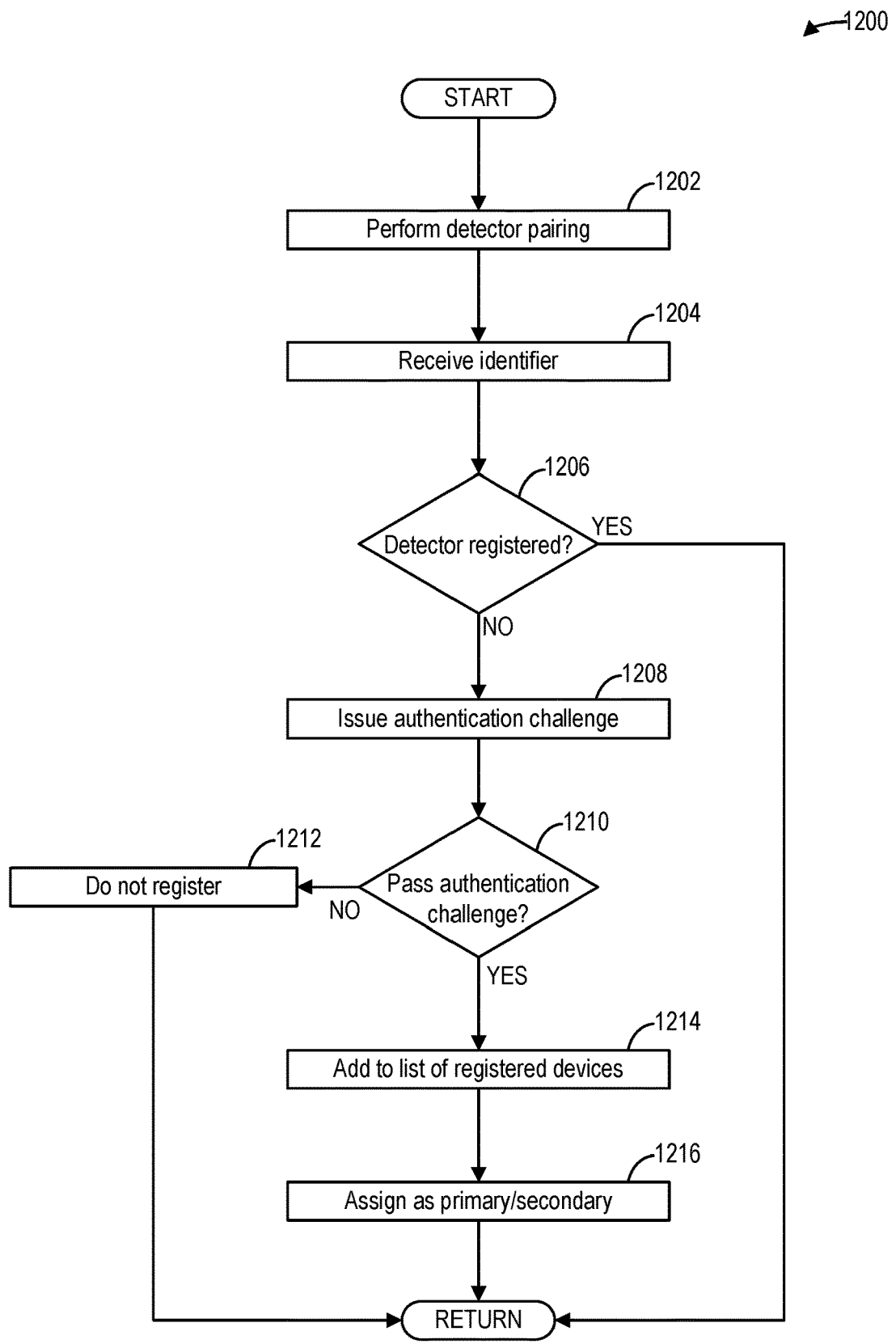
FIG. 12 shows a flowchart of a method for operating an x-ray imaging system to pair with and register a digital x-ray detector with wireless charging.

Therefore, FIG. 12 shows an example method 1200 for pairing, authenticating, and registering a digital x-ray detector of an x-ray imaging system. The x-ray imaging system may be a mobile x-ray imaging system or a stationary x-ray imaging system (e.g., such as mobile x-ray imaging system 10 of FIG. 1 or stationary x-ray imaging system 300 of FIG.

3), and may include a digital x-ray detector (e.g., as described with respect to FIGS. 4A-5). Method 1200 may be executed by a controller, such as controller 74 of FIG. 2, according to instructions stored in a memory of the controller and in conjunction with one or more inputs, such as inputs received from an operator via an operator workstation (e.g., operator workstation 34 of FIG. 2) and one or more sensors. Further, the controller may output information to the operator of the x-ray imaging system via the operator workstation and/or a display. Further, method 1200 may run during or concurrently with method 1100 of FIG. 11.

At 1202, method 1200 includes performing a detector pairing process. For example, during the detector pairing process, the x-ray imaging system may pass credentials for a secure local network connection (e.g., such as a local WLAN) to the digital x-ray detector. For example, each time the digital x-ray detector is placed in the charging area of the x-ray imaging system, the x-ray imaging system passes credentials to the detector, facilitating interchangeable detector use within a clinical environment. For example, the controller may perform the detector pairing process when a digital x-ray detector is placed in a charging area of the x-ray imaging system. In order to pair the digital x-ray detector to the x-ray imaging system, the controller may send a communication signal to the digital x-ray detector, such as an SSID and a PSK for the secure local network connection (e.g., such as a local WLAN). Sending the SSID and the PSK for the secure local network connection to the digital x-ray detector may enable the digital x-ray detector to access the secure local network connection via a long-range communication module (e.g., such as long-range communication module 516 of digital x-ray detector 402 of FIG. 5). However, until a registration and authentication process is complete, as elaborated below, the digital x-ray detector may not have full access to the local network, and may not be used to produce and transmit medical imaging data with the x-ray imaging system. For example, until the authentication process is complete, the digital x-ray detector may not communicate with the x-ray imaging system at an application layer. As another example, during the authentication and pairing process, the digital x-ray detector may communicate with the x-ray imaging system via a short-range, low data rate connection, such as NFC or Bluetooth. For example, the short-range, low data rate connection may be established by a short-range communication module (e.g., such as short-range communication module 517 of digital x-ray detector 402 of FIG. 5).

At 1204, method 1200 includes receiving an identifier. For example, via the short-range, low data connection, the controller may acquire a first identifier for the digital x-ray detector. For example, the first identifier of the digital x-ray detector may be a serial number. In one example, the controller may send a request for the identifier to the digital x-ray detector via the short-range, low data connection, and the digital x-ray detector may send the first identifier to the x-ray imaging system via the short-range, low data connection.

At 1206, method 1200 includes determining whether the paired digital x-ray detector is registered. For example, registration is a process of initially introducing the digital x-ray detector to the x-ray imaging system. As such, the paired detector may already be registered if it has previously been used with the x-ray imaging system. In order to determine whether the paired detector is registered, the controller may compare the first identifier to a list of identifiers of registered devices stored in controller memory, for example. For example, the controller may determine whether the list of identifiers of registered devices includes the first identifier.

If the controller determines that the paired digital x-ray detector is registered at 1206, method 1200 may end. For example, if the controller determines that the paired detector is registered, the controller may not register and authenticate the digital x-ray detector (e.g., because it is already registered and authenticated). As such, the paired detector may be used to collect medical imaging data, and may communicate with the x-ray imaging system at the application layer.

If the paired detector is not registered, method 1200 proceeds to 1208 and includes issuing an authentication challenge to the digital x-ray detector for authenticating the detector. For example, the controller may issue a challenge to the digital x-ray detector, and the digital x-ray detector may respond with a challenge response. In some examples, the controller may issue the challenge to the digital x-ray detector via the short-range, low-data rate connection.

At 1210, method 1200 includes determining whether the digital x-ray detector passed the authentication challenge provided at 1208. For example, based on the challenge response acquired from the digital x-ray detector, the controller may determine whether the digital x-ray detector passes the authentication challenge.

If the controller determines that the paired detector does not pass the authentication challenge at 1210, method 1200 continues to 1212 and includes not registering the paired detector. For example, the controller may not add the first identifier to a list of identifiers of registered devices, and may not assign the digital x-ray detector as one of a primary detector and a secondary detector. Further, the controller may not enable the digital x-ray detector to collect medical images. As an example, the controller may output an error message or a prompt to an operator of the x-ray imaging system. For example, the controller may prompt the user to place an approved detector in the charging area. The method may then return.

If the controller determines that the paired detector does pass the authentication challenge at 1210, method 1200 continues to 1214 and includes adding the paired detector to the list of registered devices. For example, the controller may modify the list of identifiers of registered x-ray imaging systems to include the first identifier (e.g., the identifier of the digital x-ray detector). As such, the digital x-ray detector may not be authenticated and registered upon subsequent use with the x-ray imaging system. Further, the controller may approve the digital x-ray detector to produce and transmit medical imaging data with the x-ray imaging system, and may allow the detector to communicate with the x-ray imaging system at the application level.

At 1216, method 1200 includes assigning the paired digital x-ray detector as one of a primary detector and a secondary detector. For example, the controller may acquire an operator input via the operator workstation, and may assign the paired detector as one of the primary detector and the secondary detector based on the operator input. In particular, the operator input may include designating the digital x-ray detector as one of the primary detector and the secondary detector. As another example, the controller may assign the digital x-ray detector as the primary detector if no other digital x-ray detectors are paired to the x-ray imaging system, while the controller may assign the digital x-ray detector as the secondary detector if another digital x-ray detector as assigned as the primary detector. For example, the digital x-ray detector may adjust one or more settings based on being assigned as the primary detector. As one example, the digital x-ray detector may be controlled differently based on whether it is assigned as the primary detector or the secondary detector. After 1214, method 1200 may end.

In this way, a digital x-ray detector may be wirelessly charged by an x-ray imaging system in at least two orientations. For example, by providing wireless charging to the digital x-ray detector, a cost and complexity of the x-ray imaging system may be decreased, such as by decreasing a number of physical connectors included in the x-ray imaging system. Further, decreasing a number of connectors of the x-ray imaging system and the digital x-ray detector may decrease a sanitization time for the devices. For example, by providing wireless charging to the digital x-ray detector in two distinct orientations (e.g., a first orientation and a second orientation), system flexibility may be increased. Further, the digital x-ray detector may be paired to the x-ray imaging system upon being placed in the charging area in one of the first orientation and the second orientation. As an example, upon being placed in the charging area of the x-ray imaging system, the detector may be authenticated and registered with the x-ray imaging system in order to increase network security. Registering and authenticating the digital x-ray detector may prevent non-approved devices (e.g., digital x-ray detectors not registered for use in a clinical environment) from connecting with a local network and producing medical images, which may increase network security of the clinical environment. By pairing and authenticating digital x-ray detectors, such digital x-ray detectors may be used interchangeably between a plurality of x-ray imaging systems, increasing diagnostic productivity in a clinical environment.

The technical effect of pairing with and wirelessly charging a digital x-ray detector of an x-ray imaging system is that a rechargeable battery of the digital x-ray detector may be charged without establishing a wired connection with the x-ray imaging system.

As an example, a method comprises: detecting a digital x-ray detector in a charging area of an x-ray system, the charging area including a first power source; pairing the digital x-ray detector to the x-ray system via a wireless connection with the x-ray system; and wirelessly charging the digital x-ray detector via the first power source. In the preceding example, additionally or optionally, pairing the digital x-ray detector to the x-ray system via the wireless connection with the x-ray system includes: performing a registration check; responsive to the digital x-ray detector passing the registration check, adding the digital x-ray detector to a list of approved devices and establishing a secure network connection via the wireless connection; and responsive to the digital x-ray detector not passing the registration check, displaying an error message via a display coupled to the x-ray system and not establishing the secure network connection via the wireless connection. In one or both of the preceding examples, additionally or optionally, establishing the secure network connection via the wireless connection further includes: assigning the digital x-ray detector as one of a primary detector and a secondary detector based on a user input. In any or all of the preceding examples, additionally or optionally, performing the registration check includes: acquiring a first identifier from the digital x-ray detector; determining whether the first identifier is included in a list of registered identifiers; responsive to the first identifier being included in the list of registered identifiers, determining that the digital x-ray detector passes the registration check; responsive to the first identifier not being included in a list of registered identifiers, issuing an authentication challenge to the digital x-ray detector; responsive to the digital x-ray detector responding to the authentication challenge, determining that the digital x-ray detector passes the registration check; and responsive to the digital x-ray detector not responding to the authentication challenge, determining that the digital x-ray detector does not pass the registration check. In any or all of the preceding examples, additionally or optionally, the wireless connection is one of a Near-Field Communication (NFC) protocol and a Bluetooth protocol, and the secure network connection is one of a Wi-Fi network and an Ultra-Wideband (UWB) radio protocol. In any or all of the preceding examples, additionally or optionally, the charging area further includes a second power source. In any or all of the preceding examples, the method additionally or optionally further comprises: responsive to the digital x-ray detector being in one of a first orientation relative to the first power source and a second orientation relative to the second power source, wirelessly charging the digital x-ray detector via one of the first power source and the second power source, selected based on an orientation of the digital x-ray detector. In any or all of the preceding examples, additionally or optionally, a front face of the digital x-ray detector in the first orientation is flipped about a central axis of the digital x-ray detector by 180 degrees relative to the digital x-ray detector in the second orientation, the central axis of the digital x-ray detector parallel to the front face of the digital x-ray detector.

As another example, a system comprises: a digital x-ray detector of an x-ray imaging system, the digital x-ray detector including a first module, the first module comprising a power receiver and a wireless communication unit, and the first module mechanically coupled to a first side of the digital x-ray detector; a rechargeable power storage device of the digital x-ray detector electrically coupled to the first module via a wireless power connection; and a controller for controlling the x-ray imaging system, the controller configured to be communicatively coupled to the digital x-ray detector via a short-range wireless connection, and comprising instructions in non-transitory memory that, when executed, cause the controller to: pair the digital x-ray detector to the x-ray imaging system via the short-range wireless connection; and provide wireless power to the digital x-ray detector via the wireless power connection. In the preceding example, additionally or optionally, to pair the digital x-ray detector to the x-ray imaging system, the controller includes further instructions in non-transitory memory, that, when executed, cause the controller to: acquire an identifier from the digital x-ray detector via the short-range wireless connection; responsive to a list of registered devices including the identifier, pair the digital x-ray detector to the x-ray imaging system; responsive to the list of registered devices not including the identifier, perform an authentication check; provide at least one network credential to the digital x-ray detector; configure the wireless communication unit to transmit medical imaging data to the x-ray imaging system via a high-data wireless network connection; and assign the digital x-ray detector as one of a primary detector and a secondary detector based on a user input. In one or both of the preceding examples, additionally or optionally, the system further comprises a display unit, and wherein to perform the authentication check, the controller contains further instructions that, when executed, cause the controller to: indicate that the controller is registering the digital x-ray detector via the display unit; transmit an authentication challenge to the digital x-ray detector via one of the short-range wireless connection and the high-data wireless network connection; responsive to receiving a challenge response, determine whether if the digital x-ray detector is authentic; and responsive to determining that the digital x-ray detector is authentic, add the identifier to the list of registered devices and pair the digital x-ray detector to the x-ray imaging system. In any or all of the preceding examples, additionally or optionally, the wireless power connection is between the power receiver and a wireless power source of the x-ray imaging system.

As another example, a method for an imaging system comprises: acquiring an identifier from a digital x-ray detector via a wireless connection; responsive to the identifier being one of a plurality of approved identifiers, registering the digital x-ray detector in a list of approved devices, assigning the digital x-ray detector as one of a primary detector and a secondary detector, and pairing the digital x-ray detector to the imaging system; and responsive to the identifier not being one of the plurality of approved identifiers, not registering the digital x-ray detector in the list of approved devices and displaying an error message on a display. In the preceding example, additionally or optionally, acquiring the identifier from the digital x-ray detector via the wireless connection comprises: detecting the digital x-ray detector in a charging area of the imaging system; determining the identifier based on one or more characteristics of the digital x-ray detector; issuing an authentication challenge to the digital x-ray detector via the wireless connection; and receiving a response to the authentication challenge from the digital x-ray detector via the wireless connection. In one or both of the preceding examples, the method additionally or optionally further comprises: responsive to the identifier being one of a plurality of approved identifiers, transmitting network data and power to the digital x-ray detector. In any or all of the preceding examples, additionally or optionally, transmitting network data and power to the digital x-ray detector includes: providing access to a long-range wireless network; providing power to the digital x-ray detector via a first power source, responsive to the digital x-ray detector in a first orientation; and providing power to the digital x-ray detector via a second power source, responsive to the digital x-ray detector in a second orientation. In any or all of the preceding examples, additionally or optionally, the digital x-ray detector is in the first orientation when a distance between a battery of the digital x-ray detector and the first power source is less than a distance between the battery of the digital x-ray detector and the second power source. In any or all of the preceding examples, additionally or optionally, the digital x-ray detector is in the second orientation when the distance between a battery of the digital x-ray detector and the second power source is less than the distance between the battery of the digital x-ray detector and the first power source. In any or all of the preceding examples, additionally or optionally, responsive to detecting the digital x-ray detector exiting the charging area of the imaging system, triggering a boot sequence in the digital x-ray detector via the wireless connection, the boot sequence initiating a set of instructions stored on a controller of the digital x-ray detector for acquiring x-ray images. In any or all of the preceding examples, additionally or optionally, the digital x-ray detector is assigned as one of a primary detector and a secondary detector based on a user input.

FIGS. 4A-6B show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an imaging system, comprising:
   acquiring an identifier from a digital x-ray detector via a wireless connection;
   responsive to the identifier being one of a plurality of approved identifiers, registering the digital x-ray detector in a list of approved devices, assigning the digital x-ray detector as one of a primary detector and a secondary detector, and pairing the digital x-ray detector to the imaging system; and responsive to the identifier not being one of the plurality of approved identifiers, not registering the digital x-ray detector in the list of approved devices and displaying an error message on a display.

2. The method of claim 1, wherein acquiring the identifier from the digital x-ray detector via the wireless connection comprises:
   detecting the digital x-ray detector in a charging area of the imaging system;
   determining the identifier based on one or more characteristics of the digital x-ray detector;
   issuing an authentication challenge to the digital x-ray detector via the wireless connection; and
   receiving a response to the authentication challenge from the digital x-ray detector via the wireless connection.

3. The method of claim 2 further comprising:
   responsive to the identifier being one of a plurality of approved identifiers, transmitting network data and power to the digital x-ray detector.

4. The method of claim 3, wherein transmitting network data and power to the digital x-ray detector includes:
   providing access to a long-range wireless network;
   providing power to the digital x-ray detector via a first power source, responsive to the digital x-ray detector in a first orientation; and
   providing power to the digital x-ray detector via a second power source, responsive to the digital x-ray detector in a second orientation.

5. The method of claim 4, wherein the digital x-ray detector is in the first orientation when a distance between a battery of the digital x-ray detector and the first power source is less than a distance between the battery of the digital x-ray detector and the second power source.

6. The method of claim 4, wherein the digital x-ray detector is in the second orientation when the distance between a battery of the digital x-ray detector and the second power source is less than the distance between the battery of the digital x-ray detector and the first power source.

7. The method of claim 4, wherein, responsive to detecting the digital x-ray detector exiting the charging area of the imaging system, triggering a boot sequence in the digital x-ray detector via the wireless connection, the boot sequence initiating a set of instructions stored on a controller of the digital x-ray detector for acquiring x-ray images.

8. The method of claim 1, wherein the digital x-ray detector is assigned as one of a primary detector and a secondary detector based on a user input.

* * * * *